US010125394B2

(12) United States Patent
Herold et al.

(10) Patent No.: US 10,125,394 B2
(45) Date of Patent: Nov. 13, 2018

(54) COMPOSITIONS AND METHODS FOR DIAGNOSING DISEASES AND DISORDERS ASSOCIATED WITH β CELL DEATH

(75) Inventors: Kevan C. Herold, Rowayton, CT (US); Eitan Moshe Akirav, Plainview, NY (US)

(73) Assignee: YALE UNIVERSITY, New Haven, CT (US)

( * ) Notice: Subject to any disclaimer, the term of this patent is extended or adjusted under 35 U.S.C. 154(b) by 341 days.

(21) Appl. No.: 14/127,906

(22) PCT Filed: Jun. 22, 2012

(86) PCT No.: PCT/US2012/043747
§ 371 (c)(1),
(2), (4) Date: May 28, 2014

(87) PCT Pub. No.: WO2012/178007
PCT Pub. Date: Dec. 27, 2012

(65) Prior Publication Data
US 2014/0256574 A1    Sep. 11, 2014

Related U.S. Application Data

(60) Provisional application No. 61/499,931, filed on Jun. 22, 2011, provisional application No. 61/557,085, filed on Nov. 8, 2011.

(51) Int. Cl.
*C12Q 1/6883* (2018.01)
(52) U.S. Cl.
CPC ..... *C12Q 1/6883* (2013.01); *C12Q 2600/154* (2013.01)

(58) Field of Classification Search
None
See application file for complete search history.

(56) References Cited

U.S. PATENT DOCUMENTS

2004/0171046 A1   9/2004  Berlin et al.
2007/0015156 A1   1/2007  Goggins et al.
2007/0231797 A1  10/2007  Fan et al.

FOREIGN PATENT DOCUMENTS

WO   WO 2012/097903   7/2012

OTHER PUBLICATIONS

Kuroda et al. PloS One. 2009. 4(9): e6953.*
(Continued)

*Primary Examiner* — Joseph G. Dauner
(74) *Attorney, Agent, or Firm* — Riverside Law LLP

(57) ABSTRACT

The present invention relates to compositions and methods for detecting cell death by detecting cell DNA in a biological sample. The invention relates the discovery that the presence of hypomethylated β cell DNA outside of the pancreas of a subject is indicative of β cell death. Thus, in one embodiment, the invention is a method of detecting hypomethylated β cell insulin DNA in a biological sample of a subject including the steps of: obtaining a biological sample from the subject, where the biological sample is obtained from outside of the subject's pancreas and where the biological sample contains β cell insulin DNA; determining the methylation status of at least one of the CpG dinucleotides in the β cell insulin DNA, where when at least one of the CpG dinucleotides in the β cell insulin DNA is determined to be unmethylated, the hypomethylated β cell insulin DNA is detected.

16 Claims, 10 Drawing Sheets

Specification includes a Sequence Listing.

(56) References Cited

OTHER PUBLICATIONS

Swarup et al. FEBS Letters. 2007. 581:795-799.*
Brenet et al. PloS ONE. 2011. 6(1):e14524.*
Hodges et al. Genome Research. 2009. 19:1593-1605.*
Husseiny et al. PloS ONE. 2014. 9(4):e94591.*
Fisher et al. Diabetes. 2015. 64(11):3867-3872.*
Akirav et al., 2008, Beta-Cell Mass and Type I Diabetes, Diabetes 57:2883-2888.
Snorgaard et al., 1992, Homogeneity in Pattern of Decline of Beta-cell Function in IDDM, Diabetes Care 15:1009-1013.
Steele et al., 2004, Insulin Secretion in Type I Diabetes, Diabetes 53:426-423.
Sosenko et al., 2007, A Risk Score for Type 1 Diabetes Derived From Autoantibody-Positive Participants in the Diabetes Prevention Trial—Type 1Diabetes Care 30:38-42.
Miranda et al., 2007, DNA Methylation: The Nuts and Bolts of Repression, J. Cell Physiol. 213:384-390.
Wallner et al., 2006, Methylation of Serum DNA Is an Independent Prognostic Marker in Colorectal Cancer, Clin Cancer Res. 12:7347-7352.
Muller et al., 2003, DNA Methylation in Serum of Breast Cancer Patients: An Independent Prognostic Marker, Cancer Res. 63:7641-7645.
Sherry et al., 2006, Effects of Autoimmunity and Immune Therapy on Beta-Cell Turnover in Type 1 Diabetes, Diabetes 55:3238-3245.
Berney et al., 2006, Detection of Insulin mRNA in the Peripheral Blood after Human Islet Transplantation Predicts Deterioration of Metabolic Control, Am. J. Transplant. 6:1704-1711.
Dhawan et al., 2011, Pancreatic Beta Cell Identity is Maintained by DNA Methylation-Mediated Repression of Arx, Developmental Cell, 20:419-429.
Levenson, 2010, DNA Methylation as a universal biomarker, Experi Rev Mol Diagn, 10(4):481-488.
Akirav et al., 2011, Detection of Beta Cell Death in Diabetes Using Differentially Methylated Circulating DNA, PNAS 108:19018-19023.
DNA methylation profiling identifies epigenetic dysregulation in pancreatic islets from type 2 diabetic patients By: Volkmar, Michael; Dedeurwaerder, Sarah; Cunha, Daniel A.; et al., EMBO Journal, vol. 31. Issue: 6 pp. 1405-1426 Published: Mar. 21, 2012.
Yang B T et al, "Insulin promoter DNA methylation correlates negatively with insulin gene expression and positively with HbAlevels in human pancreatic islets", Diabetologia; Clinical and Experimental Diabetes and Metabolism, Springer, Berlin, DE, (20101123), vol. 54, No. 2, doi:10.1007/S00125-010-1967-6, ISSN 1432-0428, pp. 360-367, XP019871269.

* cited by examiner

Figure 8

| Group | Primer orientation | Primer sequence | PCR conditions | SEQ ID No. |
|---|---|---|---|---|
| First-step PCR | Forward | GTGTATTTTTATTTTGTTGGTTTGTTGTT TTTTGGGAGT | 50 cycles, melting temperature 57 °C | SEQ ID 1 |
|  | Reverse | AAACTTCCTCCCAACTCCAATTATTCCACTT ATAAATCCTC |  | SEQ ID 2 |
| Real-time methylation-specific nested PCR | Common forward | TTTTGTGGTTTTATTGGTAGAG | 60 cycles, melting temperature 58.8 °C | SEQ ID 3 |
|  | Hypermethylated reverse | TTATAAATCCTCCACTTCACG |  | SEQ ID 4 |
|  | Hypomethylated reverse | TTATAAATCCTCCACTTCACA |  | SEQ ID 5 |

Figure 9

| Group | Primer orientation | Primer sequence | PCR conditions | SEQ ID No. |
|---|---|---|---|---|
| First-step PCR | Forward | TTAGGGGTTTTAAGGTAGGGTATTTGGT | 40 cycles, melting temperature 54 °C | SEQ ID 6 |
|  | Reverse | ACCAAAAACAACAATAAACAATAACT CACCTACAA |  | SEQ ID 7 |
| Real-time methylation-specific nested PCR | Methylated forward | GTGGATGCGTTTTTGTTTTGTTGGC | 50 cycles, melting temperature 64 °C | SEQ ID 8 |
|  | Methylated reverse | CACCCTACAAATCCTCTACCTCCG |  | SEQ ID 9 |
|  | Demethylated forward | TGTGGATGTGTTTTTGTTTTGTTGGT |  | SEQ ID 10 |
|  | Demethylated reverse | CACCCTACAAATCCTCTACCTCCCA |  | SEQ ID 11 |

Figure 10

| Group | Primer orientation | Primer sequence | SEQ ID No. |
|---|---|---|---|
| Primer used for mouse cloning and sequencing | Forward | GTTGGTTTTGTTTGTTTTTGGGAGTTTAAATTTATTTAGGT | SEQ ID 12 |
|  | Reverse | TTCTCCAACTAACTAATAAAAAAACAAATACTAATACAACA | SEQ ID 13 |

COMPOSITIONS AND METHODS FOR DIAGNOSING DISEASES AND DISORDERS ASSOCIATED WITH β CELL DEATH

CROSS-REFERENCE TO RELATED APPLICATIONS

This application claims the benefit of priority from U.S. Provisional Application Ser. No. 61/499,931, filed on Jun. 22, 2011, and U.S. Provisional Application Ser. No. 61/557,085, filed on Nov. 8, 2011, the entire disclosure of which is incorporated by reference herein as if set forth herein in its entirety.

BACKGROUND OF THE INVENTION

The β cell loss that leads to diabetes is silent. In type 1 diabetes mellitus (T1D), killing of β cells and subsequent presentation with hyperglycemia takes weeks in the non-obese diabetic (NOD) mouse model of T1D and possibly years in humans (Akirav et al., 2008, Diabetes 57:2883-2888). Hyperglycemia occurs when the majority of β cells have been destroyed, providing only limited options for therapy (Bluestone et al., 2010, Nature 464:1293-1300; Waldron-Lynch et al., 2009, Endocrinol. Metab. Clin. North Am. 38:303-317). Early detection of ongoing β cell death would allow for earlier interventions at a time before the development of hyperglycemia, when a more significant β cell mass is present. Indeed, immunotherapy is most successful in patients with residual β cell function (Waldron-Lynch et al., 2009, Endocrinol. Metab. Clin. North Am. 38:303-317; Bougneres et al., 1988, N. Engl. J. Med. 318: 663-670; Keymeulen et al., 2005, N. Engl. J. Med. 352: 2598-2608).

Measurements of insulin, proinsulin, and C-peptide responses to a variety of tests have been used as indices for β cell mass and destruction (Ludvigsson et al., 1982, Acta Diabetol. Lat. 19:351-358; Snorgaard et al., 1992, Diabetes Care 15:1009-1013; Greenbaum et al., 2008, Diabetes Care 31:1966-1971; Steele et al., 2004, Diabetes 53:426-423), whereas HLA genes and autoantibodies have been used as genetic indicators of high-risk individuals (Erlich et al, 2008, Diabetes 57:1084-1092; Hagopian et al., 1995, J. Clin. Invest. 95:1505-1511; Verge et al., 1996, Diabetes 45:926-933). However; these measurements do not identify the ongoing β cell destruction in islets. Unfortunately, the first direct evidence of β cell destruction becomes apparent only after β cell function has been compromised and glucose levels have risen in response to provocative stimuli or a failure of β cells to respond to increased metabolic demand and insulin resistance (Sherr et al., 2008, Nat. Clin. Pract. Endocrinol. Metab. 4:334-343; Sosenko et al., 2007, Diabetes Care 30:38-42; Polonsky et al., 1988, New Eng. J. Med. 318: 1231-9). Furthermore, the location of the pancreas in the abdominal cavity and the relatively small size of the islets of Langerhans pose a significant limitation for direct islet imaging and evaluation of β cell mass (Medarova et al., 2008, Magn. Reson. Med. 59:712-720).

Epigenetic modifications of DNA are used by various cell types to control tissue-specific gene expression. These modifications include histone acetylation/deacetylation and DNA methylation (Klose et al., 2006, Trends Biochem. Sci. 31:89-97; Bartke et al., 2010, Cell 143:470-484; Wang et al., 2007, Trends Mol. Med. 13:373-380). Methylation of DNA sequences occurs in CpG dinucleotide sites to maintain a transcriptionally repressive chromatin configuration, whereas demethylation results in a transcriptionally permissive configuration (Miranda et al., 2007, J. Cell Physiol. 213:384-390). Differential methylation of oncogenes has been used to identify microsatellite instability in patients with colon cancer, and detection of differentially methylated DNA in the serum of cancer patients has been used as a biomarker for cancer diagnosis (Grady et al., 2001, Cancer Res. 61:900-902; Wallner et al., 2006, Clin Cancer Res. 12:7347-7352; Müller et al., 2003, Cancer Res. 63:7641-7645). Previous studies have relied on the detection of serum-derived tissue-specific epigenetic modifications to identify DNA released from those cells when they die.

There is a great need in the art for compositions and methods for monitoring β cell destruction in individuals having, or at risk of developing, diabetes. The present invention addresses these needs in the art.

SUMMARY

The invention relates the discovery that the presence of hypomethylated β cell DNA outside of the pancreas of a subject is indicative of β cell death. Thus, in one embodiment, the invention is a method of detecting hypomethylated β cell insulin DNA in a biological sample of a subject including the steps of: obtaining a biological sample from the subject, where the biological sample is obtained from outside of the subject's pancreas, and where the biological sample contains β cell insulin DNA; determining the methylation status of at least one of the CpG dinucleotides in the β cell insulin DNA, where when at least one of the CpG dinucleotides in the β cell insulin DNA is determined to be unmethylated, the hypomethylated β cell insulin DNA is detected.

In another embodiment, the invention is a method of detecting β cell death by detecting hypomethylated β cell insulin DNA in a subject, where when at least one of the CpG dinucleotides in the β cell insulin DNA is determined to be unmethylated, β cell death is detected. In a further embodiment, the invention is a method of measuring the level of β cell death by detecting hypomethylated β cell insulin DNA in a subject according to the method of claim 1, where the amount of hypomethylated β cell insulin DNA is quantified, and where a higher amount of hypomethylated β cell insulin DNA indicates a higher level of β cell death.

In one embodiment, the invention is a method of diagnosing a subject with a disease or disorder associated with β cell death by detecting hypomethylated β cell insulin DNA, where when hypomethylated β cell insulin DNA is detected, a disease or disorder associated with β cell death in the subject is diagnosed. In various embodiments, the disease or disorder diagnosable by the methods of the invention include pre-diabetes mellitus, diabetes mellitus, diabetes mellitus type 1, diabetes mellitus type 2, and gestational diabetes.

In another embodiment, the invention is a method of assessing the severity of a disease or disorder associated with β cell death in a subject by detecting hypomethylated β cell insulin DNA, where the amount of hypomethylated β cell insulin DNA is quantified, and where a higher quantity of hypomethylated β cell insulin DNA indicates a greater severity of the disease or disorder in the subject. In various embodiments, the disease or disorder diagnosable by the methods of the invention include pre-diabetes mellitus, diabetes mellitus, diabetes mellitus type 1, diabetes mellitus type 2, and gestational diabetes.

In a further embodiment, the invention is a method of monitoring the progression of a disease or disorder associated with β cell death in a subject by detecting hypomethylated β cell insulin DNA in the subject, where when the amount of hypomethylated β cell insulin DNA detected at a first time point is different than the amount of hypomethylated β cell insulin DNA detected at a second time point, the difference in the amount of hypomethylated β cell insulin DNA is an indicator of the progression of the disease or disorder associated with β cell death in the subject. In various embodiments, the disease or disorder diagnosable by the methods of the invention include pre-diabetes mellitus, diabetes mellitus, diabetes mellitus type 1, diabetes mellitus type 2, and gestational diabetes.

In one embodiment, the invention is a method of monitoring the effect of a therapeutic regimen on a disease or disorder associated with β cell death in a subject by detecting hypomethylated β cell insulin DNA in the subject, where when the amount of hypomethylated β cell insulin DNA detected before therapeutic regimen is applied is different than the amount of hypomethylated β cell insulin DNA detected during or after the therapeutic regimen is applied, the difference in the amount of hypomethylated β cell insulin DNA is an indicator of the effect of the therapeutic regimen on the disease or disorder associated with β cell death in the subject. In various embodiments, the disease or disorder diagnosable by the methods of the invention include pre-diabetes mellitus, diabetes mellitus, diabetes mellitus type 1, diabetes mellitus type 2, and gestational diabetes.

In another embodiment, the invention is a method of assessing the post-operative prognosis of a β cell transplant, islet transplant, or pancreas transplant by detecting hypomethylated β cell insulin DNA in a subject, where the amount of hypomethylated β cell insulin DNA is quantified, and the amount of hypomethylated β cell insulin DNA is a measure of the prognosis of a β cell transplant, islet transplant, or pancreas transplant subject.

In one embodiment, the invention is a kit for detecting hypomethylated β cell insulin DNA in a biological sample obtained from outside the pancreas of a subject, including: at least one reagent or device for isolating β cell insulin DNA from the biological sample; at least one reagent or device for determining the methylation status of the β cell insulin DNA isolated from the biological sample; at least one comparator; and instructions for the preparation, performance, and analysis of the determination of methylation status of the β cell insulin DNA isolated from the biological sample.

In another embodiment, the invention is a composition comprising a biomarker, where the biomarker comprises an isolated hypomethylated β cell insulin DNA, or fragment thereof, where the isolated hypomethylated β cell insulin DNA was isolated from a biological sample obtained from a subject outside of the subject's pancreas.

In a further embodiment, the invention is a composition comprising an amplicon, where the amplicon was produced by PCR using at least one primer that hybridizes to a template comprising an isolated hypomethylated β cell insulin DNA, or fragment thereof, where the isolated hypomethylated β cell insulin DNA was isolated from a biological sample obtained from a subject outside of the subject's pancreas. In some embodiments, the at least one primer has a nucleic acid sequence selected from the group consisting of: SEQ ID NO: 1 and 2. In other embodiments, the at least one primer has a nucleic acid sequence selected from the group consisting of: SEQ ID NO: 8-11.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1B, is a schematic depicting DNA sequences from βTC3 (SEQ ID NO:16) and PMJ (SEQ ID NO:15) cell lines and β and non-β cells having a differentially methylated CpG dinucleotide in the Ins1 gene. FIG. 1A is a representation of unmodified DNA sequence (SEQ ID NO: 14) of murine Ins1 DNA depicting the position of the 20 differentially methylated CpG dinucleotide (arrow, upper region) and a comparison of bisulfite treated genomic DNA from either the βTC3 or PMJ cell line, demonstrating the nucleotide modification of CpG dinucleotides due to demethylation at position 523393278 (lower region). FIG. 1B is a representation of the sequence analysis of product amplified in the first-step PCR. The sequence of 15 clones from murine β cells and 8 clones from murine liver cells are shown (○ indicates demethylated cytosines; ● indicates methylated cytosines). The locations of the methylation sites from the transcription start site are indicated. The primers of the second-step PCR were specific for methylated/demethylated cytosine at nucleotide position +177, corresponding to nucleotide 52339278.

FIGS. 3A-3D, depicts the results of experiments demonstrating that demethylated Ins1 DNA is enriched in primary islets and FACS-sorted primary insulin-positive cells. FIG. 3A is a graph depicting the ratio of demethylated:methylated DNA in primary murine tissues. The cycle differences were normalized to the cycle difference of kidney DNA. The data are from a single experiment representative of more than five experiments. FIG. 3B is a FACS plot analysis showing the presence of insulin-positive and insulin-negative cells sorted from dispersed islets. FIG. 3C is a graph depicting the demethylated:methylated DNA levels in the sorted cell population (shown in FIG. 3B). The insulin-positive cell cycle difference was normalized to the insulin-negative cell cycle difference. Data are from a single experiment representative of two experiments. FIG. 3D is a graph depicting DNA from the first-step reactions from sorted β cells and from islet-derived non-β cells, which were mixed in ratios of 1:1, 1:10, and 1:100 and then added to the second-step reaction. The relationship between the ratio of DNA and the demethylation index is shown (2=0.96; P=0.0038).

FIGS. 4A-4D, depicts the results of experiments demonstrating the increase of demethylated Ins1 DNA in the serum after STZ treatment of mice. FIG. 4A is a graph depicting blood glucose levels of untreated and STZ-injected BALB/c mice (n=6 animals per group)*P<0.05; ±P<0.02 vs. prediabetic mice. FIG. 4B is a graph depicting the demethylation index of the nested PCR performed on DNA from sera of the BALB/c mice. Between 16 and 18 mice were analyzed at each time point. The sera from two mice were pooled for analysis. *P<0.05. The box-and-whisker plots show the minimum and maximum values. FIG. 4C is a graph depicting the histomorphic analysis of DAPI-positive, insulin-positive cells in the islets of the STZ-treated mice shown in B. *P<0.0001; ±P<0.002. FIG. 4D is a series of images of representative islets of STZ-treated mice, stained for DAPI and insulin.

FIG. 5, comprising FIG. 5A is a graph depicting IPGTT data for prediabetic NOD mice at various ages (n≥5 per group). Note that the fasting glucose (at t=0) is similar at all time-points. FIG. 5B is a graph depicting the area under the curve of IPGTT data from FIG. 5A. *P<0.05. FIG. 5C is a graph depicting the demethylation index measured with DNA from the sera of prediabetic (week 7-14) and diabetic NOD mice. P=0.0002 by ANOVA; **P<0.01; *P<0.05; n=5, 5, 5, 7, and 5 mice/group. The box-and-whisker plots show the minimum and maximum values. FIG. 5D is a graph depicting the results of an experiment where pancreata and serum were harvested from mice at the indicated ages (n=5 mice per time point) for measurement of insulin content. FIG. 5E is a graph depicting the relationship between pancreatic insulin content and demethylation index in individual mice. Two measurements from each mouse are plotted ($r^2$=0.28; P<0.05). In this experiment, pancreata and serum were harvested from mice at the indicated ages (n=5 mice per time point) for measurement of demethylation index. The insulin content and demethylation index in 11- and 15-wk-old mice were compared with 7-wk-old mice. *P<0.05; **P<0.02 by post hoc analysis of ANOVA.

FIGS. 6A-6E, depicts the results of an analysis of insulin DNA sequences in human tissues and sera. FIG. 6A is an illustration of the unmodified DNA sequence in human Ins gene showing the preserved CpG pair at nucleotide positions (SEQ ID NO: 17) +273 and (SEQ ID NO: 18) +399 identified in the UCSC Genome Browser (genome.ucsc.edulcgi-bin/hgGateway). FIG. 6B is an illustration depicting the sequence data of the first-step PCR showing methylation DNA patterns in primary human kidney and whole islets. The arrow shows the presence of demethylated CpG found in human islets at nucleotide position +399 (at position 2182036, site of the reverse primer). Note the two peaks in human islets representing both demethylated and methylated forms from β cells and non-β cells in the islets. FIG. 6C is an illustration depicting the sequence analysis of product amplified in the first-step PCR from sorted human β cells and kidney. The sequence of 10 clones from human β cells and 12 clones from human kidney cells are shown (○ indicates demethylated cytosines; ● indicates methylated cytosines). The base pairs are indicated downstream from the transcription start site. The primers of the second-step PCR were specific for methylated/demethylated cytosine at nucleotide position +273 and +399. FIG. 6D is a graph depicting DNA isolated from human kidney, liver, and islets and analyzed by nested PCR. Synthetic DNA was also analyzed in these reactions. Each dot represents a separate isolation and analysis of tissue DNA. The demethylation index was significantly greater with DNA from islets compared with liver and kidney. ***P<0.001. FIG. 6E is a graph showing the demethylation index of DNA isolated from five subjects with recent-onset T1D (●) and from six healthy control subjects (■). The demethylation index was significantly higher in patients with T1D (P=0.017, Mann-Whitney U test).

FIG. 8 is a table depicting the primer sequences and PCR conditions used for studies of murine Ins1.

FIG. 9 is a table depicting the primer sequences and PCR conditions used for studies of human Ins.

FIG. 10 is a table depicting the primer sequences used for cloning and sequencing of murine Ins1.

DETAILED DESCRIPTION

Figure 1:
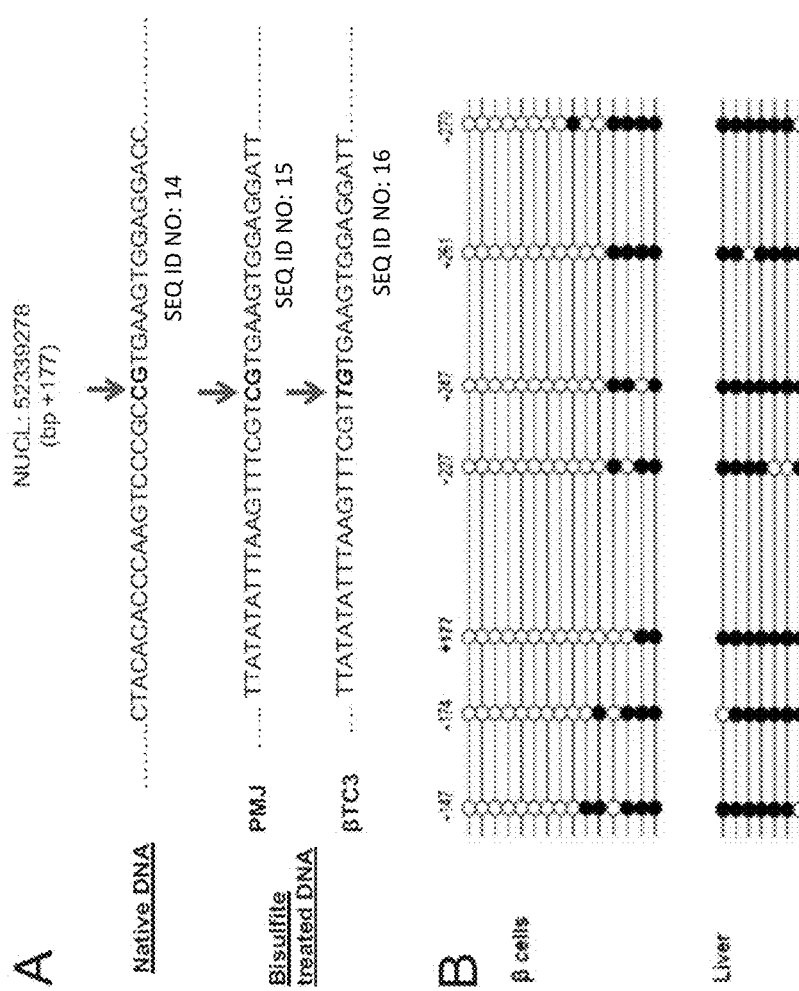
FIG. 1, comprising

The invention relates the discovery that the presence of hypomethylated β cell DNA outside of the pancreas of a subject is indicative of β cell death. Thus, the invention relates to compositions and methods useful for assessing the extent of methylation of β cell DNA, for detecting the presence of hypomethylated β cell DNA outside of the pancreas of a subject as an indicator of β cell death, for assessing the level of hypomethylated β cell DNA present outside of the pancreas of a subject as a measure of β cell death, for diagnosing a disease or disorder associated with β cell death, for monitoring the progression of a disease or disorder associated with β cell death, for assessing the severity of a disease or disorder associated with β cell death, for selecting a treatment regimen to treat a disease or disorder associated with β cell death, for assessing the post-operative prognosis of a β cell transplant, islet transplant, or pancreas transplant subject, and for monitoring the effect of a treatment of a disease or disorder associated with β cell death.

In one embodiment, the presence of hypomethylated β cell DNA outside of the pancreas of a subject is detected in a biological sample obtained from the subject. In some embodiments, the biological sample is a bodily fluid. In certain embodiments, the biological sample is blood, serum or plasma.

In some embodiments, the disease or disorder associated with β cell death is pre-diabetes mellitus, diabetes mellitus, diabetes mellitus type 1, diabetes mellitus type 2, or gestational diabetes.

In one embodiment, the hypomethylated β cell DNA is insulin gene DNA (such as, murine Ins1 or human Ins). In various embodiments, the hypomethylated insulin DNA is hypomethylated within at least one of a regulatory region, an intron, an exon, a non-coding region, or a coding region.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

An "amplicon" as used herein, refers to the amplification product of a nucleic acid amplification reaction, such as PCR.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, or the frequency with which such a sign or symptom is experienced by a subject, or both, is reduced.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

As used herein "hypomethylated" means that the extent of methylation of a target nucleic acid (such as genomic DNA) is lower than it could be (i.e., a DNA or DNA fragment in which many or most of the CpG dinucleotides are not methylated). By way of a non-limiting example, a hypomethylated nucleic acid is a nucleic acid that is less methylated than it could be, because less than all of the potential methylation sites of the nucleic acid are methylated. By way of another non-limiting example, a hypomethylated nucleic acid, such as the insulin gene, is a nucleic acid that is less methylated in a cell type that expresses the nucleic acid (e.g., β cells), as compared with a cell type that does not express the nucleic acid (e.g., liver cell). Thus, by way of one non-limiting example, a hypomethylated β cell insulin DNA has less than all of the potential methylation sites methylated and is less methylated as compared with a liver cell insulin DNA.

As used herein, an "instructional material" includes a publication, a recording, a diagram, or any other medium of expression which can be used to communicate the usefulness of a compound, composition, method, assay, vector, or delivery system of the invention in a kit. Optionally, or alternately, the instructional material can describe one or more methods of detecting, assessing or alleviating a disease or disorder in a cell or a tissue of a mammal. The instructional material of the kit of the invention can, for example, be affixed to a container which contains the identified compound, composition, assay components, vector, or delivery system of the invention or be shipped together with a container which contains the identified compound, composition, assay components, vector, or delivery system. Alternatively, the instructional material can be shipped separately from the container with the intention that the instructional material and the compound be used cooperatively by the recipient.

The term "microarray" refers broadly to both "DNA microarrays" and "DNA chip(s)," and encompasses all art-recognized solid supports, and all art-recognized methods for affixing nucleic acid molecules thereto.

The terms "patient," "subject," "individual," and the like are used interchangeably herein, and refer to any animal, or cells thereof whether in vitro or in situ, amenable to the compositions or methods described herein. In certain non-limiting embodiments, the patient, subject or individual is a human.

A "therapeutic" treatment is a treatment administered to a subject who exhibits signs or symptoms of a disease or disorder, for the purpose of diminishing or eliminating those signs or symptoms.

As used herein, "treating a disease or disorder" means reducing or eliminating the severity or frequency of a sign or symptom of a disease or disorder experienced by a subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates the discovery that the presence of hypomethylated β cell DNA outside of the pancreas of a subject is indicative of β cell death. Thus, the invention relates to compositions and methods useful for assessing the extent of methylation of β cell DNA, for detecting the presence of hypomethylated β cell DNA outside of the pancreas of a subject as an indicator of β cell death, for assessing the level of hypomethylated β cell DNA present outside of the pancreas of a subject as a measure of β cell death, for diagnosing a disease or disorder associated with β cell death, for monitoring the progression of a disease or disorder associated with β cell death, for assessing the severity of a disease or disorder associated with β cell death, for selecting a treatment regimen to treat a disease or disorder associated with β cell death, for assessing the post-operative prognosis of a β cell transplant, islet transplant, or pancreas transplant subject, and for monitoring the effect of a treatment of a disease or disorder associated with β cell death.

It is an advantage of the present invention that β cell death can be detected non-invasively and earlier in the pathological process than other available methods for detecting diseases and disorders associated with β cell death, thereby allowing for earlier diagnosis and therapeutic intervention of the pathologic process.

In one embodiment, the presence of hypomethylated β cell specific DNA outside of the pancreas of a subject is detected in a biological sample obtained from the subject. In some embodiments, the biological sample is a bodily fluid. In certain embodiments, the biological sample is blood, serum or plasma.

In some embodiments, the disease or disorder associated with β cell death is pre-diabetes mellitus, diabetes mellitus, diabetes mellitus type 1, diabetes mellitus type 2, or gestational diabetes.

In one embodiment, the hypomethylated β cell DNA is insulin gene DNA (such as, murine Ins1 or human Ins). In various embodiments, the hypomethylated insulin DNA is hypomethylated within at least one of a regulatory region, an intron, an exon, a non-coding region, or a coding region.

In one embodiment, the hypomethylated β cell DNA is at least some portion of insulin gene DNA (such as, murine Ins1 or human Ins). In various embodiments, the hypomethylated insulin DNA is hypomethylated within at least one of a regulatory region, an intron, an exon, a non-coding region, or a coding region. In various embodiments, the hypomethylated insulin DNA is unmethylated on at least one of the CpG dinucleotides at nucleotide positions 255, 273, 303, 329, 364, 370, 396, and 399 of the human insulin gene (Ins).

Methods

In various embodiments, the invention is a method useful for assessing whether a subject has hypomethylated β cell specific DNA present outside of the subject's pancreas. In the various methods of the invention described herein, the methods involve the detection of hypomethylated β cell insulin DNA in a biological sample of a subject, including the steps of: obtaining a biological sample from the subject, wherein the biological sample is obtained from outside of the subject's pancreas, and wherein the biological sample contains β cell insulin DNA; determining the methylation status of at least one of the CpG dinucleotides in the β cell insulin DNA, wherein when at least one of the CpG dinucleotides in the β cell insulin DNA is determined to be unmethylated, the hypomethylated β cell insulin DNA is detected.

The present invention relates the discovery that the presence of hypomethylated β cell specific DNA outside of the pancreas of a subject is indicative of a disease or disorder associated with β cell death. Epigenetic modifications of DNA are used by various different types of cells to control gene expression, including tissue-specific gene expression. Non-limiting examples of epigenetic modifications affecting gene expression include histone acetylation/deacetylation and DNA methylation. Methylation of DNA sequences occurs in CpG dinucleotide sites to maintain a transcriptionally repressive chromatin configuration, whereas demethylation results in a transcriptionally permissive configuration. β cells express insulin and thus maintain a transcriptionally permissive hypomethylated insulin gene, as compared with other types of cells that do not express insulin. Therefore, as described herein throughout, the presence of hypomethylated insulin DNA found outside the pancreas of a subject is indicative of β cell death resulting in the release of this hypomethylated insulin gene DNA from dead and dying β cells.

In one embodiment, the invention is a method for assessing the extent of methylation of hypomethylated β cell DNA in a biological sample obtained from a subject. The assessment of the extent of methylation of hypomethylated β cell DNA by the method of the invention is useful to assess the extent of methylation of any hypomethylated β cell DNA. In one embodiment, the hypomethylated β cell DNA is at least some fragment of the insulin gene. In various embodiments, the hypomethylated insulin DNA is hypomethylated within at least one of a regulatory region, an intron, an exon, a non-coding region, or a coding region. In some embodiments, the extent of methylation of the hypomethylated (cell insulin gene DNA is compared with the extent of methylation of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the extent of methylation is assessed using methylation-specific PCR, a methylation-specific DNA microarray, bisulfite sequencing, pyrosequencing of bisulfite treated DNA, or combinations thereof. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In another embodiment, the invention is a method of detecting hypomethylated β cell DNA outside of the pancreas of a subject, in a biological sample obtained from a subject, as an indicator of β cell death. The method of detecting hypomethylated β cell DNA of the invention is useful for detecting any hypomethylated β cell DNA. In one embodiment, the detected hypomethylated β cell DNA is at least some fragment of the insulin gene. In various embodiments, the detected hypomethylated insulin DNA is hypomethylated within at least one of a regulatory region, an intron, an exon, a non-coding region, or a coding region. In some embodiments, the extent of methylation of the detected hypomethylated (cell insulin gene DNA is compared with the extent of methylation of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the hypomethylated β cell DNA is detected using methylation-specific PCR, a methylation-specific DNA microarray, bisulfite sequencing, pyrosequencing of bisulfite treated DNA, or combinations thereof. In one embodiment, the biological sample is a bodily fluid. In various embodiments, the biological sample is at least one of plasma, serum or blood. In some embodiments, the amount of hypomethylated β cell DNA detected outside of the pancreas of the subject is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In a further embodiment, the invention is a method of assessing the level of hypomethylated β cell DNA present outside of the pancreas of a subject, in a biological sample obtained from a subject, as a measure of β cell death. The method of assessing the level of hypomethylated β cell DNA by the method of the invention is useful for assessing the level of any hypomethylated β cell DNA. In one embodiment, the assessed hypomethylated β cell DNA is at least some fragment of the insulin gene. In various embodiments, the assessed hypomethylated insulin DNA is hypomethylated within at least one of a regulatory region, an intron, an exon, a non-coding region, or a coding region. In some embodiments, the level of the hypomethylated β cell insulin gene DNA is compared with the level of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the level of hypomethylated β cell DNA is assessed using methylation-specific PCR, a methylation-specific DNA microarray, bisulfite sequencing, pyrosequencing of bisulfite treated DNA, or combinations thereof. In one embodiment, the biological sample is a bodily fluid. In various embodiments, the biological sample is at least one of plasma, serum or blood. In some embodiments, the amount of hypomethylated β cell DNA detected outside of the pancreas of the subject is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In one embodiment, the invention is a method of diagnosing a disease or disorder associated with β cell death, by detecting the presence of, or assessing the level of, hypomethylated β cell DNA present outside of the pancreas of a subject, in a biological sample obtained from a subject. The method of diagnosing a disease or disorder associated with β cell death, by detecting the presence of, or assessing the level of, hypomethylated β cell DNA by the method of the invention is useful for detecting or assessing the level of any hypomethylated β cell DNA. In one embodiment, the hypomethylated β cell DNA is at least some fragment of the insulin gene. In various embodiments, the hypomethylated insulin DNA is hypomethylated within at least one of a regulatory region, an intron, an exon, a non-coding region, or a coding region. In some embodiments, the level of the hypomethylated β cell insulin gene DNA is compared with the level of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the level of hypomethylated β cell DNA is assessed using methylation-specific PCR, a methylation-specific DNA microarray, bisulfite sequencing, pyrosequencing of bisulfite treated DNA, or combinations thereof. In one embodiment, the biological sample is a bodily fluid. In various embodiments, the biological sample is at least one of plasma, serum or blood. The diseases or disorders associated with β cell death diagnosable using the methods of the invention include pre-diabetes mellitus, diabetes mellitus, diabetes mellitus type 1, diabetes mellitus type 2, gestational diabetes, or combinations thereof. In some embodiments, the amount of hypomethylated β cell DNA detected outside of the pancreas of the subject is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In another embodiment, the invention is a method of monitoring the progression of a disease or disorder associated with β cell death, by detecting the presence of, or assessing the level of, hypomethylated β cell DNA present outside of the pancreas of a subject, in a biological sample obtained from a subject. The method of monitoring the progression of a disease or disorder associated with β cell death, by detecting the presence of, or assessing the level of, hypomethylated β cell DNA by the method of the invention is useful for detecting or assessing the level of any hypomethylated β cell DNA. In one embodiment, the hypomethylated β cell DNA is at least some fragment of the insulin gene. In various embodiments, the hypomethylated insulin DNA is hypomethylated within at least one of a regulatory region, an intron, an exon, a non-coding region, or a coding region. In some embodiments, the level of the hypomethylated β cell insulin gene DNA is compared with the level of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the level of hypomethylated β cell DNA is assessed using methylation-specific PCR, a methylation-specific DNA microarray, bisulfite sequencing, pyrosequencing of bisulfite treated DNA, or combinations thereof. In one embodiment, the biological sample is a bodily fluid. In various embodiments, the biological sample is at least one of plasma, serum or blood. The diseases or disorders associated with β cell death monitorable using the methods of the invention include pre-diabetes mellitus, diabetes mellitus, diabetes mellitus type 1, diabetes mellitus type 2, gestational diabetes, or combinations thereof. In some embodiments, the amount of hypomethylated β cell DNA detected outside of the pancreas of the subject is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In a further embodiment, the invention is a method of assessing the severity of a disease or disorder associated with β cell death, by detecting the presence of, or assessing the level of, hypomethylated β cell DNA present outside of the pancreas of a subject, in a biological sample obtained from a subject. The method of assessing the severity of a disease or disorder associated with β cell death, by detecting the presence of, or assessing the level of, hypomethylated β cell DNA by the method of the invention is useful for detecting or assessing the level of any hypomethylated β cell DNA. By way of one non-limiting example, the higher the level of hypomethylated β cell DNA present outside of the pancreas of a subject, the greater the severity of the disease or disorder. By way of another non-limiting example, the lower the level of hypomethylated β cell DNA present outside of the pancreas of a subject, the lower the severity of the disease or disorder. In one embodiment, the hypomethylated β cell DNA is at least some fragment of the insulin gene. In various embodiments, the hypomethylated insulin DNA is hypomethylated within at least one of a regulatory region, an intron, an exon, a non-coding region, or a coding region. In some embodiments, the level of the hypomethylated β cell insulin gene DNA is compared with the level of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the level of hypomethylated β cell DNA is assessed using methylation-specific PCR, a methylation-specific DNA microarray, bisulfite sequencing, pyrosequencing of bisulfite treated DNA, or combinations thereof. In one embodiment, the biological sample is a bodily fluid. In various embodiments, the biological sample is at least one of plasma, serum or blood. The diseases or disorders associated with β cell death assessable using the methods of the invention include pre-diabetes mellitus, diabetes mellitus, diabetes mellitus type 1, diabetes mellitus type 2, gestational diabetes, or combinations thereof. In some embodiments, the amount of hypomethylated β cell DNA detected outside of the pancreas of the subject is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In one embodiment, the invention is a method of assessing the post-operative prognosis of a β cell transplant, an islet transplant subject, or a pancreas transplant subject, by detecting the presence of, or assessing the level of, hypomethylated β cell DNA present outside of the pancreas of a subject, in a biological sample obtained from a subject. The method of assessing the post-operative prognosis of a β cell transplant, an islet transplant subject, or a pancreas transplant subject, by detecting the presence of, or assessing the level of, hypomethylated β cell DNA by the method of the invention is useful for detecting or assessing the level of any hypomethylated β cell DNA. In one embodiment, the hypomethylated β cell DNA is at least some fragment of the insulin gene. In various embodiments, the hypomethylated insulin DNA is hypomethylated within at least one of a regulatory region, an intron, an exon, a non-coding region, or a coding region. In some embodiments, the level of the hypomethylated β cell insulin gene DNA is compared with the level of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the level of hypomethylated β cell DNA is assessed using methylation-specific PCR, a methylation-specific DNA microarray, bisulfite sequencing, pyrosequencing of bisulfite treated DNA, or combinations thereof. In one embodiment, the biological sample is a bodily fluid. In various embodiments, the biological sample is at least one of plasma, serum or blood. In some embodiments, the amount of hypomethylated β cell DNA detected outside of the pancreas of the subject is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In another embodiment, the invention is a method of selecting a treatment regimen to treat a disease or disorder associated with β cell death, by detecting the presence of, or assessing the level of, hypomethylated β cell DNA present outside of the pancreas of a subject, in a biological sample obtained from a subject. The method of selecting a treatment regimen to treat a disease or disorder associated with β cell death, by detecting the presence of, or assessing the level of, hypomethylated β cell DNA by the method of the invention is useful for detecting or assessing the level of any hypomethylated β cell DNA. In one embodiment, the hypomethylated β cell DNA is at least some fragment of the insulin gene. In various embodiments, the hypomethylated insulin DNA is hypomethylated within at least one of a regulatory region, an intron, an exon, a non-coding region, or a coding region. In some embodiments, the level of the hypomethylated β cell insulin gene DNA is compared with the level of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the level of hypomethylated β cell DNA is assessed using methylation-specific PCR, a methylation-specific DNA microarray, bisulfite sequencing, pyrosequencing of bisulfite treated DNA, or combinations thereof. In one embodiment, the biological sample is a bodily fluid. In various embodiments, the biological sample is at least one of plasma, serum or blood. The diseases or disorders associated with β cell death for which treatment regimens can be selected using the methods of the invention include pre-diabetes mellitus, diabetes mellitus, diabetes mellitus type 1, diabetes mellitus type 2, gestational diabetes, or combinations thereof. In some embodiments, the amount of hypomethylated β cell DNA detected outside of the pancreas of the subject is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In another embodiment, the invention is a method of monitoring the effect of a treatment of a disease or disorder associated with β cell death, by detecting the presence of, or assessing the level of, hypomethylated β cell DNA present outside of the pancreas of a subject, in a biological sample obtained from a subject, before, during and after a treatment is administered. The method of monitor a treatment of a disease or disorder associated with β cell death, by detecting the presence of, or assessing the level of, hypomethylated β cell DNA by the method of the invention is useful for detecting or assessing the level of any hypomethylated β cell DNA. In one embodiment, the hypomethylated β cell DNA is at least some fragment of the insulin gene. In various embodiments, the hypomethylated insulin DNA is hypomethylated within at least one of a regulatory region, an intron, an exon, a non-coding region, or a coding region. In some embodiments, the level of the hypomethylated β cell insulin gene DNA is compared with the level of the insulin gene DNA of a comparator cell type which does not express insulin. Non-limiting examples of comparator cell types useful in the methods of the invention include liver cells and kidney cells. In various embodiments, the hypomethylated insulin DNA is unmethylated on at least one of the CpG dinucleotides at nucleotide positions 255, 273, 303, 329, 364, 370, 396, 399 of the human insulin gene (Ins). In various embodiments, the level of hypomethylated β cell DNA is assessed using methylation-specific PCR, a methylation-specific DNA microarray, bisulfite sequencing, pyrosequencing of bisulfite treated DNA, or combinations thereof. In one embodiment, the biological sample is a bodily fluid. In various embodiments, the biological sample is at least one of plasma, serum or blood. The diseases or disorders associated with β cell death for which treatments can be monitored using the methods of the invention include pre-diabetes mellitus, diabetes mellitus, diabetes mellitus type 1, diabetes mellitus type 2, gestational diabetes, or combinations thereof. In some embodiments, the amount of hypomethylated β cell DNA detected outside of the pancreas of the subject is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

In the various methods of the invention, the level of the hypomethylated β cell DNA present outside of the pancreas of a subject is compared with a comparator control. By way of non-limiting examples, a comparator control useful in the methods of the invention include a positive control, a negative control, a historical control, a historical norm, or the level of a reference molecule present in the biological sample.

In various embodiments, the subject is a human subject, and may be of any race, sex and age. Representative subjects include those who are suspected of having experienced β cell death, those who have been diagnosed as having experienced β cell death, those who have been diagnosed as having a disease or disorder associated with β cell death, those who at risk of a recurrence of β cell death, and those who are at risk of developing a disease or disorder associated with β cell death.

Information obtained from the methods of the invention described herein can be stored in a manipulatable database that can be used for the analysis, diagnosis, prognosis, monitoring, assessment, treatment planning, treatment selection and treatment modification of diseases and disorders associated with β cell death. Thus, the invention also includes such databases and their methods of use.

A biological sample can be obtained by appropriate methods, such as, by way of examples, biopsy or fluid draw. In certain embodiments, a biological sample containing genomic DNA is used. The biological sample can be used as the test sample; alternatively, the biological sample can be processed to enhance access to nucleic acids (e.g., nucleic acids comprising methylated or unmethylated nucleotides), or copies of nucleic acids (e.g., copies of nucleic acids comprising methylated or unmethylated nucleotides), and the processed biological sample can then be used as the test sample. For example, in various embodiments, nucleic acid is prepared from a biological sample. Alternatively, or in addition, an amplification method can be used to amplify nucleic acids comprising all or a fragment of the nucleic acid in a biological sample, for use as the test sample in the assessment for the presence or absence of methylation.

There are many methods known in the art for the determination of the methylation status of a target nucleic acid and new methods are continually reported. In some embodiments, hybridization methods, such as Southern analysis, can be used (see Current Protocols in Molecular Biology, 2012, Ausubel, F. et al., eds., John Wiley & Sons, including all supplements). For example, methylation-specific restriction enzymes can be used to digest DNA, cleaving at specific sites depending upon methylation status, followed by hybridization with a nucleic acid probe. A "nucleic acid probe," as used herein, can be a DNA probe or an RNA probe; the nucleic acid probe can contain at least one polymorphism of interest, as described herein. The probe can be, for example, the gene, a gene fragment (e.g., one or more exons), a vector comprising the gene, a probe or primer, etc. For representative examples of use of nucleic acid probes, see, for example, U.S. Pat. Nos. 5,288,611 and 4,851,330.

A preferred probe for detecting DNA is a labeled nucleic acid probe capable of hybridizing to target DNA. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target DNA. The hybridization sample is maintained under conditions which are sufficient to allow specific hybridization of the nucleic acid probe to DNA. Specific hybridization can be performed under high stringency conditions or moderate stringency conditions, as appropriate. In a preferred embodiment, the hybridization conditions for specific hybridization are high stringency. Specific hybridization, if present, is then detected using standard methods. More than one nucleic acid probe can also be used concurrently in this method. Specific hybridization of any one of the nucleic acid probes is indicative of the presence of the target DNA of interest.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a target nucleic acid sequence. Hybridization of the PNA probe to a target nucleic acid sequence is indicative of the presence of the target nucleic acid.

In another embodiment of the methods of the invention, analysis by methylation sensitive restriction enzymes can be used to detect the methylation status of a target nucleic acid, if the methylation status results in the creation or elimination of a restriction site. A sample containing nucleic acid from the subject is used. RFLP analysis is conducted as described (see Current Protocols in Molecular Biology, supra). The digestion pattern of the relevant fragments indicates the presence or absence of methylation.

Various methods are available for determining the methylation status of a target nucleic acid. (See, for example, Rapley and Harbron, 2011, Molecular Analysis and Genome Discovery, John Wiley & Sons; Tollefsbol, 2010, Handbook of Epigenetics: The New Molecular and Medical Genetics, Academic Press). For example, direct sequence analysis can be used in the methods of the invention to detect the methylation status of a target nucleic acid. For example, bisulfite-treated DNA utilizing PCR and standard dideoxynucleotide DNA sequencing can directly determine nucleotides that are resistant to bisulfite conversion. (See, for example, Frommer et al., 1992, PNAS 89:1827-1831). Briefly, in an example direct sequencing method, primers are designed that are strand-specific as well as bisulfite-specific (e.g., primers containing non-CpG cytosines so that they are not complementary to non-bisulfite-treated DNA), flanking the potential methylation site. Such primers will amplify both methylated and unmethylated sequences. Pyrosequencing can also be used in the methods of the invention to detect the methylation status of a target nucleic acid. Briefly, in an example pyrosequencing method, following PCR amplification of the region of interest, pyrosequencing is used to determine the bisulfite-converted sequence of specific CpG dinucleotide sites in the target nucleic. (See, for example, Tost et al., 2003, BioTechniques 35:152-156; Wong et al., 2006, 41:734-739).

A microarray methylation assay can also be used in the methods of the invention to detect the methylation status of a target nucleic acid. Briefly, target nucleic acids are treated with bisulfite, amplified, hybridized to probes, labeled and detected. (See, for example, Wang and Petronis, 2008, DNA Methylation Microarrays: Experimental Design and Statistical Analysis; Weisenberger et al., 2008, Comprehensive DNA Methylation Analysis on the Illumina Infinium Assay Platform). For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

Methylation specific PCR can also be used in the methods of the invention to detect the methylation status of a target nucleic acid. Briefly, sets of PCR primers are designed that will hybridize specifically to either methylated nucleotides or unmethylated nucleotides, after their modification by bisulfite treatment. (See, for example, Yuryev, 2007, PCR Primer Design, Volume 402, Chapter 19, Humana Press; Esteller, 2005, DNA Methylation: Approaches, Methods, and Applications, CRC Press). Non-limiting examples of primers useful in the methods of the invention included the primers exemplified by SEQ ID NOS: 1-11. The PCR process is well known in the art (U.S. Pat. No. 4,683,195, U.S. Pat. No. 4,683,202, and U.S. Pat. No. 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed before. Most preferably the detection of the duplex is done using at least one primer directed to the target nucleic acid. In yet another embodiment of PCR, the detection of the hybridized duplex comprises electrophoretic gel separation followed by dye-based visualization.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer.

Among the conditions of stringency is the melting temperature (Tm) for the amplification step using the set of primers, which is in the range of about 55° C. to about 70° C. Preferably, the Tm for the amplification step is in the range of about 59° C. to about 72° C. Most preferably, the Tm for the amplification step is about 60° C.

Typical hybridization and washing stringency conditions depend in part on the size (i.e., number of nucleotides in length) of the DNA or the oligonucleotide probe, the base composition and monovalent and divalent cation concentrations (Ausubel et al., 1994, eds Current Protocols in Molecular Biology).

In a preferred embodiment, the process for determining the quantitative and qualitative profile according to the present invention is characterized in that the amplifications are real-time amplifications performed using a labeled probe, preferably a labeled hydrolysis-probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 65° C. to 75° C. Preferably, the Tm for any one of the hydrolysis-probes of the present invention is in the range of about 67° C. to about 70° C. Most preferably, the Tm applied for any one of the hydrolysis-probes of the present invention is about 67° C.

In another preferred embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target flanking nucleotide sequence In another aspect, the length of the primer can vary in length, preferably about 15 to 28 nucleotides in length (e.g., 16, 17, 18, 19, 20, 21, 22, 23, 24, 25, 26, or 27 nucleotides in length).

A target nucleic acid, and PCR or other appropriate methods can be used to amplify all or a fragment of the nucleic acid, and/or its flanking sequences, if desired. The methylation status of the nucleic acid, or a fragment thereof (e.g., one or more exons, one or more introns, one or more intragenic regions, one or more regulatory regions, etc.), is determined, using methods elsewhere described herein or otherwise known in the art. The technique used to determine the methylation status of the target nucleic acid can vary in the methods of the invention, so long as the methylation status of the target nucleic acid is determined. In various embodiments of the invention, the methylation status of a target nucleic acid is compared with the methylation status of a comparator nucleic acid.

The probes and primers useful in the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}$P, $^{33}$P, $^{35}$S or $^{3}$H. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the biological sample using known techniques. The nucleic acid can be double-stranded or single-stranded (i.e., a sense or an antisense single strand) and can be complementary to a nucleic acid encoding a polypeptide. The nucleic acid content may also be a DNA extraction performed on a fresh or fixed biological sample.

Routine methods also can be used to extract genomic DNA from a biological sample, including, for example, phenol extraction. Alternatively, genomic DNA can be extracted with kits such as the QIAamp™. Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

Compositions

The invention relates the discovery that the presence of hypomethylated β cell DNA outside of the pancreas of a subject serves as a biomarker of β cell death, as well as diseases and disorders associated with β cell death. Thus, the invention relates to isolated biomarker compositions, isolated from the subject outside of the subject's pancreas. Such biomarkers are useful for screening and diagnosing, as well as assessing the effect of an applied therapy. The biomarker compositions of the invention provide a non-invasive means of detecting β cell death, at an earlier time in the progression of the diseases and disorders associated with 3 cell death than currently available diagnostics are capable of. The biomarker compositions disclosed herein may be used in combination with existing clinical diagnostic measures of β cell death and associated diseases and disorders.

The invention also includes compositions comprising amplicons produced by the methods described elsewhere herein using as a template the hypomethylated β cell DNA comprising at least some portion of insulin gene DNA (such as, murine Ins1 or human Ins), which was isolated from a biological sample obtained from the subject outside of the subject's pancreas. In some embodiments, the hypomethylated β cell DNA used as a template to produce the amplicons of the invention is treated with bisulfite. In some embodiments, the hypomethylated β cell insulin DNA used as template to produce the amplicons of the invention is unmethylated on at least one of the CpG dinucleotides at nucleotide positions 255, 273, 303, 329, 364, 370, 396, and 399 of the human insulin gene (Ins). In some embodiments, the amplicons of the invention are produced in PCR reaction using at least one of the primers exemplified by SEQ ID NOS: 1 and 2. In other embodiments, the amplicons of the invention are produced in PCR reaction using at least one of the primers exemplified by SEQ ID NOS: 2, 3, 4 and 5. In some embodiments, the amplicons of the invention are produced in PCR reaction using at least one of the primers exemplified by SEQ ID NOS: 6 and 7. In other embodiments, the amplicons of the invention are produced in PCR reaction using at least one of the primers exemplified by SEQ ID NOS: 8, 9, 10 and 11.

Kits

The present invention also pertains to kits useful in the methods of the invention described elsewhere herein. Such kits comprise components useful in any of the methods described herein, including for example, hybridization probes or primers (e.g., labeled probes or primers), reagents for detection of labeled molecules, restriction enzymes, allele-specific oligonucleotides, means for amplification of a subject's nucleic acid, means for analyzing a subject's nucleic acid, negative comparator standards, positive comparator standards, and instructional materials. For example, in one embodiment, the kit comprises components useful for analysis of the methylation status of nucleic acids in a biological sample obtained from a subject outside of the subject's pancreas.

A variety of kits having different components are contemplated by the current invention. Generally, the invention provides a kit comprising a component for detecting or quantifying methylation status of a nucleic acid obtained from the subject. In another embodiment, the kit comprises a component for collecting a biological sample, such as bodily fluid, from the subject. In another embodiment, the kit comprises instructions for use of the kit contents.

In one embodiment, the kit comprises a means to detect the methylation status of a hypomethylated β cell DNA. In another embodiment, the kit comprises a means to quantify the level of hypomethylated β cell DNA present in the subject, outside of the subject's pancreas.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Detection of β Cell Death in Diabetes Using Differentially Methylated Circulating DNA Described herein are methods for the in vivo detection of β cell death in autoimmune and chemically-induced diabetes in mice, in humans, in human tissues, and in serum from patients with T1D. The methods identify a methylated CpG dinucleotide in insulin DNA that is derived exclusively from β cells. The data described herein indicate that the method provides a biomarker for detecting β cell loss in prediabetic subjects during progression of diabetes, as well as in subjects with new-onset T1D. Demethylation of CpG sites in the insulin promoter has previously been identified (Kuroda et al., 2009, PLoS. ONE 4:e6953), consistent with the notion that methylation of promoters is a mechanism for controlling tissue-specific gene expression. However, the studies described herein targeted differentially methylated CpG dinucleotides in the Ins1 gene in mice and the Ins gene in humans. Although not wishing to be bound by any particular theory, the conservation of demethylation of this sequence across species is consistent with the explanation that its methylation plays an active role in the regulation of insulin gene transcription. In addition, via sequencing, it was shown that CpG sites both upstream and downstream of the CpG at +177 are also equally demethylated in β cell DNA, implicating the entire region in gene regulation.

Sequence analyses revealed that unlike human Ins, which was completely demethylated in primary β cells, murine Ins1 was demethylated in 75% of the CpG sites studied from murine β cells isolated from MIP-GFP$^+$ mice.

Acute β cell death in vivo was detected, as indicated by the presence of β cell-derived demethylated DNA after STZ treatment. The fact that hyperglycemia was not observed at the 8 hour time-point demonstrates the ability of the present method to detect β cell death before frank hyperglycemia occurs. This conclusion is supported by the histomorphic analysis of the percentage of nucleated cells in the islet, which revealed a drop in the percentage of DAPI-positive, insulin-positive cells, consistent with the explanation that DNA material is released to the surrounding tissues and can be detected in the circulation.

Interestingly, the measure of β cell death demonstrated continued release of demethylated insulin DNA after the appearance of frank hyperglycemia, but at a reduced level compared with prediabetic (i.e., 14-week-old) mice. The decline in β cell-derived DNA after the onset of hyperglycemia is consistent with the explanation that the relative abundance of demethylated insulin DNA in the circulation may be reduced because of a total loss of β cell mass. For example, a higher percentage of β cells may be destroyed after diagnosis with hyperglycemia than before diagnosis, but fewer β cells actually may be destroyed (Sherry et al., 2006, Diabetes 55:3238-3245; Basadonna et al., 1988, Am. J. Surg. 156:191-193; Berney et al., 2006, Am. J. Transplant. 6:1704-1711).

The present method useful in mice was also useful for detecting circulating β cell-derived DNA in humans. Uniform demethylation of CpG sites within the insulin gene in human β cells and methylation in non-β cells was found. Tissue analysis findings were consistent with this finding from the sequence analysis. Importantly, the average demethylation index was significantly greater in subjects with new-onset T1D, in whom β cell death occurs, than in healthy control subjects.

The materials and methods employed in these experiments are now described.

Mice

Female NOD/LtJ, MIP-GFP NOD, and BALB/c mice were obtained from The Jackson Laboratory and maintained under pathogen-free conditions. Seven-week-old NOD mice were screened for hyperglycemia every 2 weeks and were diagnosed with diabetes when two consecutive glucose levels >200 mg/dL were measured in whole blood from the tail vein using a Bayer Glucometer Elite XL. The animal care protocol was approved by Yale University's Animal Use Committee.

Human Subjects

Tissues were obtained from the pathology laboratory at Yale New Haven Hospital. Serum was collected from healthy control subjects and from individuals with recent-onset (i.e., within the first 1½ y) T1D participating in a clinical trial (NCT 00378508). Institutional Review Board approval was obtained for the collection of tissues and sera, and informed consent was obtained from subjects for the collection of sera.

STZ Treatment

Eight-week-old BALB/c mice received a single i.p. injection of 200 mg/kg of STZ. Blood glucose levels were measured at 8 hours and 24 hours after STZ treatment. At designated time points, mice were killed and serum and pancreas were collected for further analysis.

Insulin Content of Pancreas

Whole pancreas was snap-frozen in liquid nitrogen (Best et al., 1939, J. Physiol 97:107-119). Insulin was extracted with precooled (−20° C.) acid-ethanol, and the insulin content was measured with a mouse insulin ELISA kit (Crystal Chem, Downers Grove, Ill.).

DNA Collection and Bisulfite Treatment

For isolation of purified β cells, islets were isolated from NOD/SCID mice, and single cell suspensions were prepared by collagenase digestion. The cells were stained intracellularly with guinea pig anti-insulin antibodies, followed by a secondary FITC-conjugated donkey anti-guinea pig antibody. The stained cells were then FACS-sorted into either insulin-positive or insulin-negative fractions. Other β cells were isolated from islets from NOD MIP-GFP mice, and insulin-positive cells were sorted on the basis of GFP fluorescence. Purified human β cells were isolated from dissociated islets that were permeabilized and stained with FluoZin-3-AM (Jayaraman, 2011, Curr. Protoc. Cytom. 55:6.27.1-6.27-16). The β cells were sorted by gating on the upper 16% of the stained cells. DNA from tissue, cells, and serum samples was purified using the Qiagen QIAamp DNA Blood Kit following the manufacturer-recommended protocol. Synthetic unmethylated and methylated DNA was purchased from Millipore (Billerica, Mass.). Purified DNA was quantitated using a NanoDrop 2000 spectrophotometer. DNA was then subjected to bisulfite treatment and purified on a DNA binding column to remove excessive bisulfite reagent using the Zymo EZ DNA Methylation Kit.

First-Step PCR and Gel Extraction

A methylation-independent reaction was carried out to increase the amount of DNA template for PCR analysis. The forward and reverse primers and melting temperatures for the murine and human insulin genes are listed in FIG. 8 and FIG. 9. For the reaction, bisulfite-treated DNA template was added to Zymo Taq Premix. The PCR conditions for murine and human reactions are given in FIG. 8 and FIG. 9. The PCR products were excised from a 3% agarose gel. Negative controls without DNA did not yield products in the first-step reaction. In certain experiments, the purified product was sequenced at Yale University's Keck Biotechnology Research Laboratory.

Cloning and Sequencing of Insulin DNA

PCR products obtained using methylation-independent primers (from sorted β cells, pancreatic islet cells, and control tissue, either kidney or liver) were purified using a Qiagen PCR Purification Kit and ligated via TOPO-TA cloning into the pCR2.1-TOPO vector (Invitrogen, Grand Island, N.Y.). For the mouse sequence, primers outside the region in the nested PCR reactions (FIG. 10) were used to increase the number of CG sites. Competent TOP-10 bacteria cells were transformed with the products of TOPO ligation and streaked onto agar plates (ampicillin-resistance). After overnight incubation at 37° C., between 12 and 40 colonies from each ligation were picked with clean pipette tips and individually inoculated into 96-well plates. After culture, the bacteria were lysed and used as template DNA for real-time PCR with SYBR Green with the methylation-independent primers. Productive ligations were identified based on Ct values and melting points. The PCR products were sequenced by the Keck Biotechnology Research Laboratory.

Nested Methylation-Dependent Real-Time PCR

Gel-purified PCR products were used as a template for a quantitative PCR with primers specific for demethylated and methylated insulin 1 DNA. The conditions for the reaction with SYBR Green (Qiagen) and primers are listed in FIG. 8. The reaction was performed on an iQ-5 multicolor real-time PCR system (Bio-Rad), and the Ct cycle was determined for reactions with the demethylated and methylated primer pairs (FIG. 8). The relative abundance of demethylated DNA was expressed using the following equation: demethylation index=$2^{(methylated\ cycle\ number)-(demethylated\ cycle\ number)}$. In some experiments (FIG. 3A and FIG. 3C), the ratio of the demethylation index between tissues is presented. The second-step reaction Ct values were between 15 and 40.

Immunofluorescence

Pancreas was resected and fixed for 24 hours in 2% PFA, then placed in a sucrose gradient and snap-frozen in liquid nitrogen. Noncontiguous 14-μm pancreatic sections were stained with antibodies to insulin (Invitrogen) and DAPI. The bound anti-insulin antibody was detected by immunofluorescent secondary antibodies (Jackson Immunoresearch). The slides were analyzed by fluorescence microscopy using an Olympus BX-51 microscope. Image analysis and postprocessing were performed using ImageJ (rsb.info.nih.gov/ij/). Numbers of single- and dual-color-labeled cells were counted using functions in ImageJ (colocalization, watershed, and analyze particles) (Collins, 2007, Biotechniques 43 (Suppl. 1):25-30).

Statistical Analyses

Data are expressed as mean±SEM. The differences between means and the effects of treatments were analyzed by one-way ANOVA with Tukey's post hoc test using Prism 5 (GraphPad software) to identify the significance (P<0.05) for all pairs of combinations. Nonnormally distributed data were analyzed using nonparametric tests.

The results of this example are now described.

Methylation-Specific Primers can Detect Differentially Methylated Ins1 Gene DNA from βTC3 and PMJ Murine Cell Lines To identify differentially methylated CpG dinucleotides present in the Ins1 gene in β cells, the methylation patterns of the Ins1 gene in the glucose-responsive murine insulinoma cell line βTC3 were examined (Poitout et al., 1995, Diabetes 44:306-313). As a non-β cell control, the PMJ macrophage cell line was used. DNA from both cell types was extracted and subjected to bisulfite treatment as described below. A differentially methylated CpG dinucleotide at position NUCL:52339278 (genome.ucsc.edu/cgi-bin/hgGateway, February 2009 GRCh37/hg19) on chromosome 19 was identified, corresponding to the CpG in position +177 downstream from the Ins1 transcription start site, which was demethylated in βTC3 cells and methylated in control PMJ cells (FIG. 1A). This CpG dinucleotide is located in the coding region of the insulin mRNA residing in the proinsulin protein and is evolutionarily conserved in mouse and human insulin genes.

Figure 2:
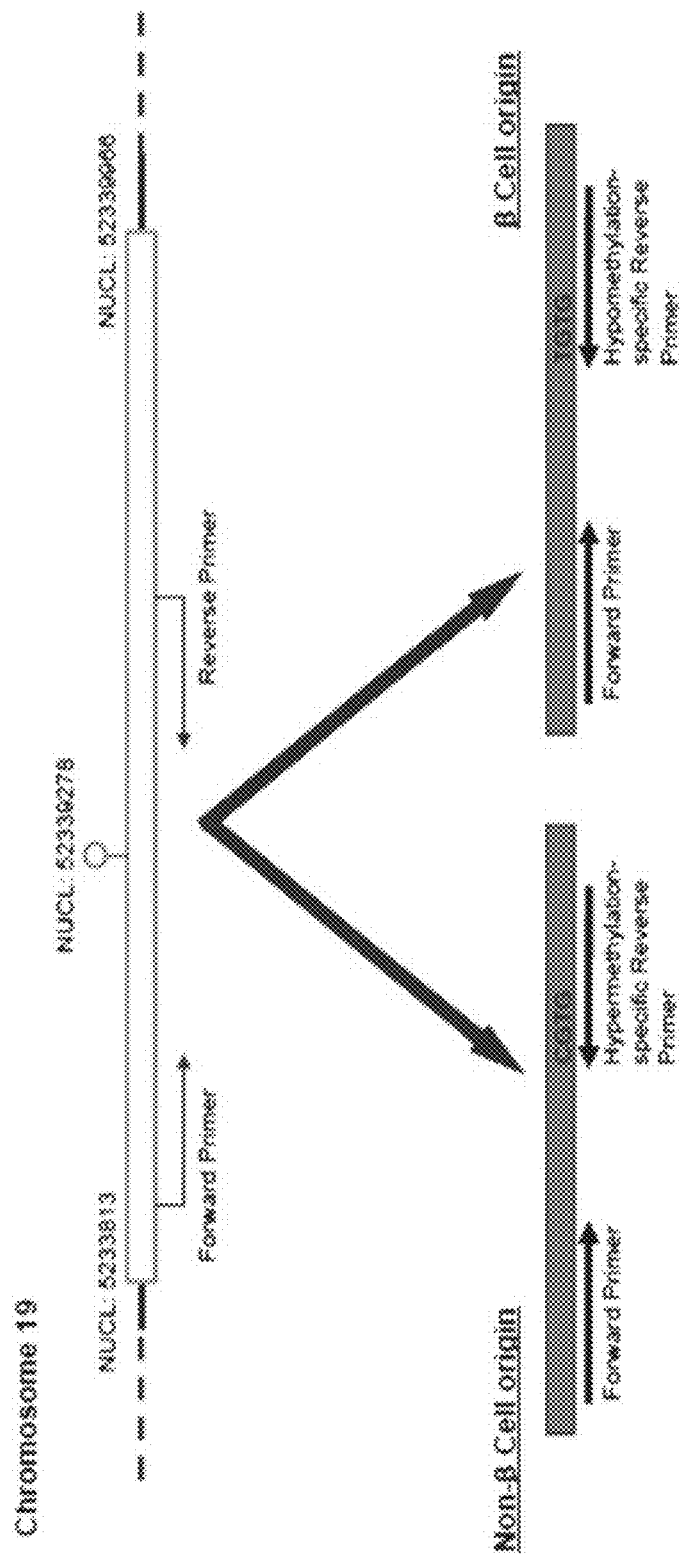
FIG. 2 is a schematic depicting the methods used to identify differentially methylated DNA using real-time PCR. Bisulfite-treated purified DNA from tissues, cells, or serum was purified and used in the first-step, methylation-insensitive reaction. The products were gel-purified and used as a template in a second-step reaction with methylation-specific primers.

To verify the tissue specificity of demethylation at this site, the frequency of demethylated and methylated CpG sites was determined in products of the methylation-insensitive PCR from bisulfite-treated DNA from sorted murine insulin-positive cells isolated from MIP-GFP mice and from liver (FIG. 1B). The majority of the sites were demethylated in DNA from β cells. The CpG site at +177 was demethylated in 13 of 15 clones isolated from β cells, but in 0 of 8 clones isolated from liver (P<0.001). It was found that 25% of the 105 sites, or 33% of the clones, showed methylated cytosines in at least one of the seven CpG sites analyzed. In contrast, 86% of the 56 sites analyzed from liver were methylated. The relatively low amounts of circulating DNA in the serum posed a challenge for detecting cell-specific DNA species. Thus, a nested PCR was designed in which insulin DNA with methylation-insensitive primers was first amplified between a region spanning the CpG dinucleotide of interest, followed by a second reaction with methylation-specific primers capable of differentiating β cell-derived and non-β cell-derived insulin DNA (FIG. 2A and FIG. 8). The first PCR generated a product of 204 bp that was gel-extracted to improve real-time PCR efficiency. This first-step product was used as template in a second PCR with methylation site-specific primers. Real-time PCR analysis showed a 256-fold (eight-cycle) increase in demethylated DNA levels relative to methylated DNA levels in bisulfite-treated DNA from βTC3 cells with a single melting peak (FIG. 2B). An exact inverse ratio was observed in the non-β cell line PMJ, in which PCR product from methylation-dependent primers was observed eight cycles earlier than PCR product from methylation-independent primers. The identity of the PCR products was verified by sequencing. Taken together, these data indicate the presence of a unique differentially methylated CpG dinucleotide in the coding region of the Ins1 gene, and demonstrate the ability to detect differentially methylated DNA from either a β cell-like or non-β cell-like origin by methylation-specific quantitative PCR analysis.

Demethylated Ins1 DNA is Enriched in Primary Murine Islets and Cell-Sorted Insulin-Positive Cells To assess the assay's ability to detect methylation-specific modification of DNA from primary murine tissues, kidney, liver, brain, and islet tissues were collected from NOD/SCID mice, which, unlike WT NOD mice, do not develop insulitis or β cell destruction. DNA was extracted and treated with bisulfite, followed by the nested PCR analysis described above. Methylation-specific primers demonstrated a >12-fold increase in demethylated DNA in the crude islet preparations compared with liver, kidney, and brain (FIG. 3A).

To confirm that β cells were the primary source of the demethylated insulin DNA in our nested PCR, murine islets were dissociated into single cells and stained for insulin. Insulin-positive β cells and insulin-negative cells were sorted by FACS (FIG. 3B), and the DNA was isolated and treated as described above. There was a 45-fold increase in demethylated DNA in the insulin-positive cell fraction compared with insulin-negative cells from islets (FIG. 3C). Product sequencing revealed an identical demethylated modification in insulin-positive islet cells as in the βTC3 cell line, whereas the non-β cell fraction demonstrated a methylated CpG dinucleotide, as observed in the PMJ cell line.

Figure 3:
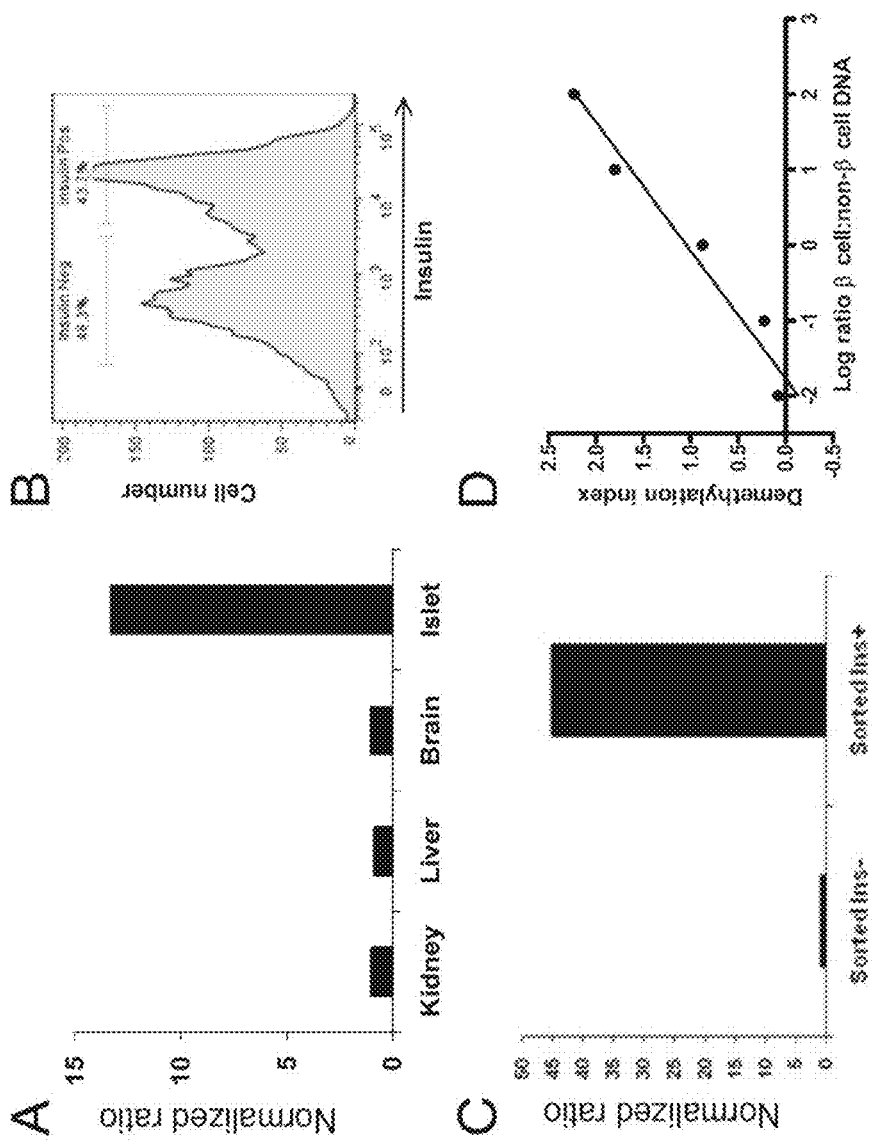
FIG. 3, comprising

The ratio between the two DNA species was next analyzed by mixing demethylated DNA (derived from β cells) and methylated DNA (derived from non-β cells) and measuring the difference in cycle threshold (Ct) values detected (FIG. 3D). The difference in the Ct values of the methylated and demethylated products of the second-step PCR were characterized using the demethylation index as below, which corresponds to quantitative differences in the quantity of DNA. There was a linear relationship between the log ratio of β cell-derived and non-β cell-derived DNA and a demethylation index between 100:1 and 1:100 (r2=0.957; P<0.01), suggesting that it is possible to measure the quantitative differences in the DNA species over this wide range.

Figure 4:
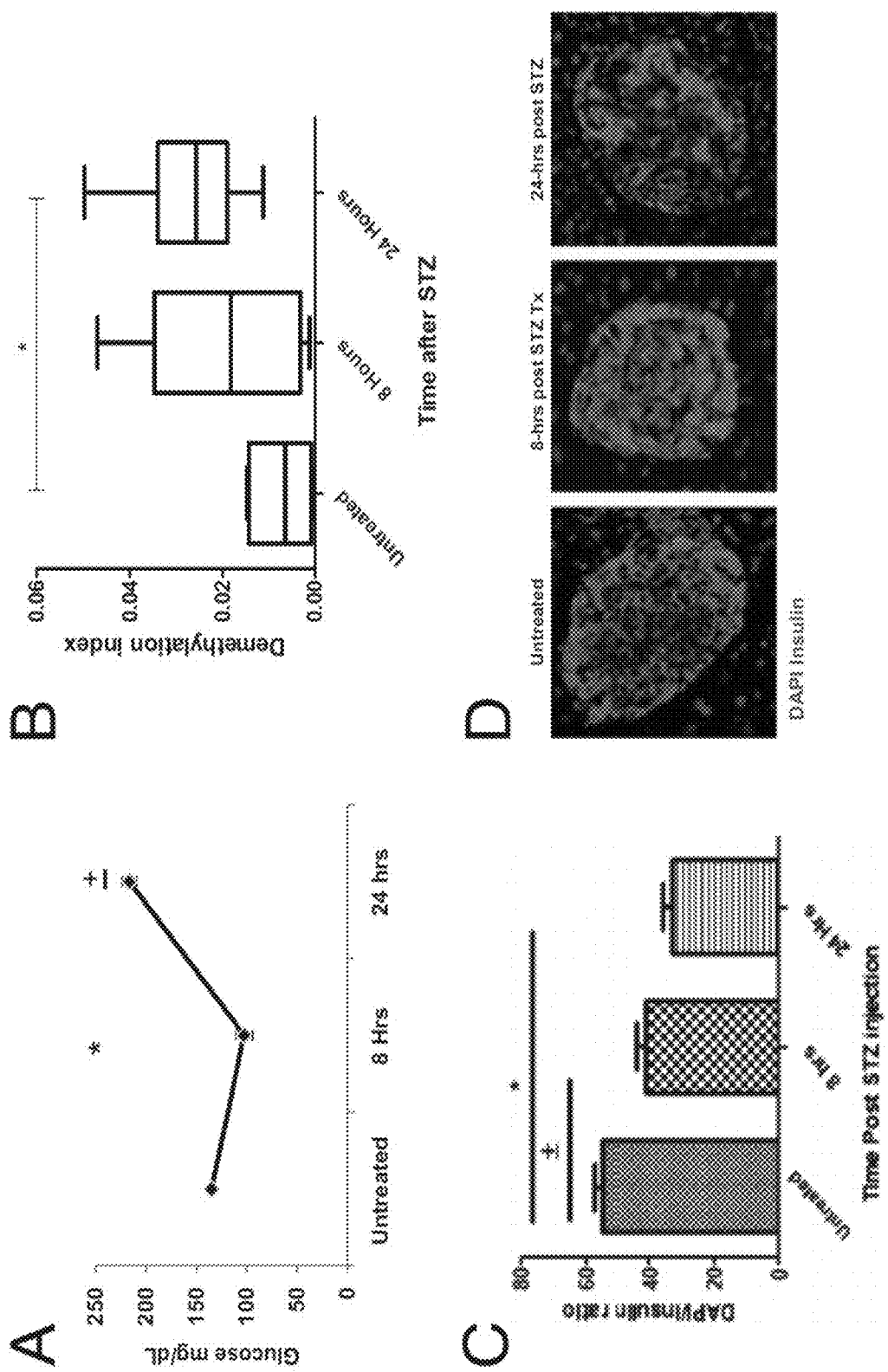
FIG. 4, comprising

Circulating Demethylated Ins1 DNA is Increased in Streptozotocin-Treated BALB/c Mice To determine whether the assay can detect β cell death in vivo, serum was collected from BALB/c mice before and after treatment with high-dose (200 mg/kg) streptozotocin (STZ), and the DNA was isolated, processed, and analyzed as described above. The STZ-treated mice demonstrated increased glucose levels at 24 hours after STZ injection, indicating acute injury to β cells (P<0.001) (FIG. 4A). Despite a modest decline in glucose levels at 8 hours after treatment (P<0.05), most likely reflecting loss of β cell membrane integrity and release of insulin granules, there was a 2.6-fold increase in the demethylation index at 8 hours (P<0.05) and a 3.8-fold increase at 24 hours (P<0.02) (FIG. 3C). The percentage of nucleated cells in the islets after STZ treatment was studied and a reduced percentage of DAPI-positive, insulin-positive cells staining in the islets at 8 hours after STZ treatment was found (UnTx=55.1% vs. $t_8$=41.3%; P<0.002) (FIG. 3D). A further reduction in the percentage of DAPI-positive, insulin-positive cells was found at 24 hours after STZ treatment (FIG. 3C), which corresponded to the peak in circulating demethylated DNA and increased baseline glucose levels (UnTx=55.1% vs. $t_{24}$=32.8%; P<0.0001) (FIG. 3B). Taken together, these data indicate the ability of methylation-specific real-time PCR to detect demethylated DNA derived from damaged β cells in the serum of STZ-treated mice.

Circulating Demethylated Ins1 DNA is Elevated in Prediabetic NOD Mice

Figures 5A, 5B:
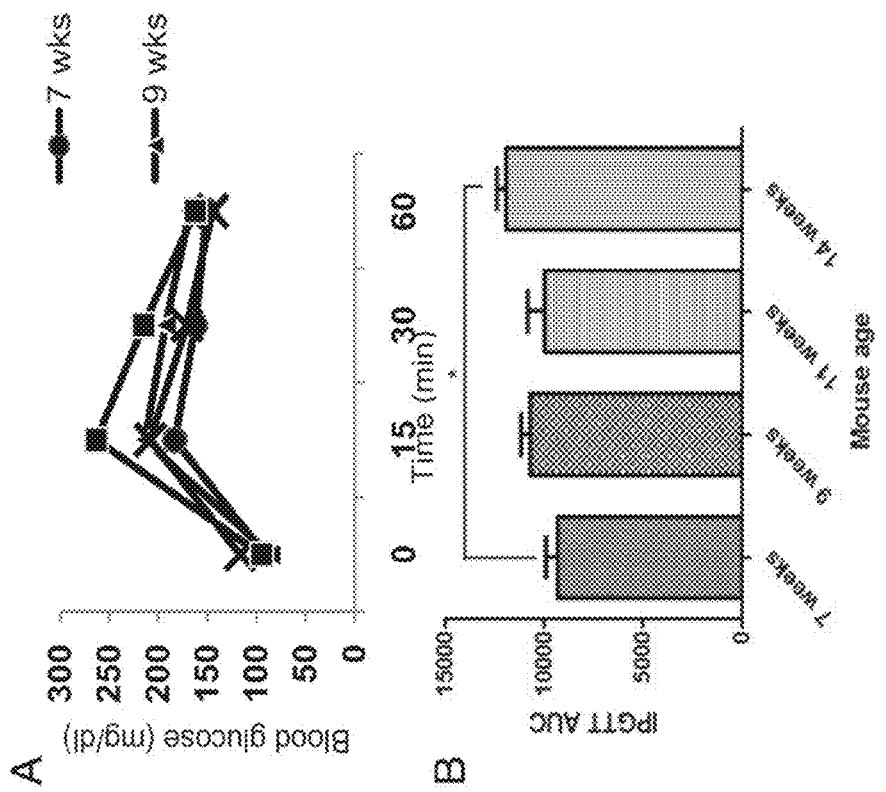
FIGS. 5A-5E, depicts the results of experiments demonstrating the increase in serum-derived demethylated Ins1DNA in prediabetic NOD mice with impaired glucose tolerance.
Figures 5C, 5D, 5E:
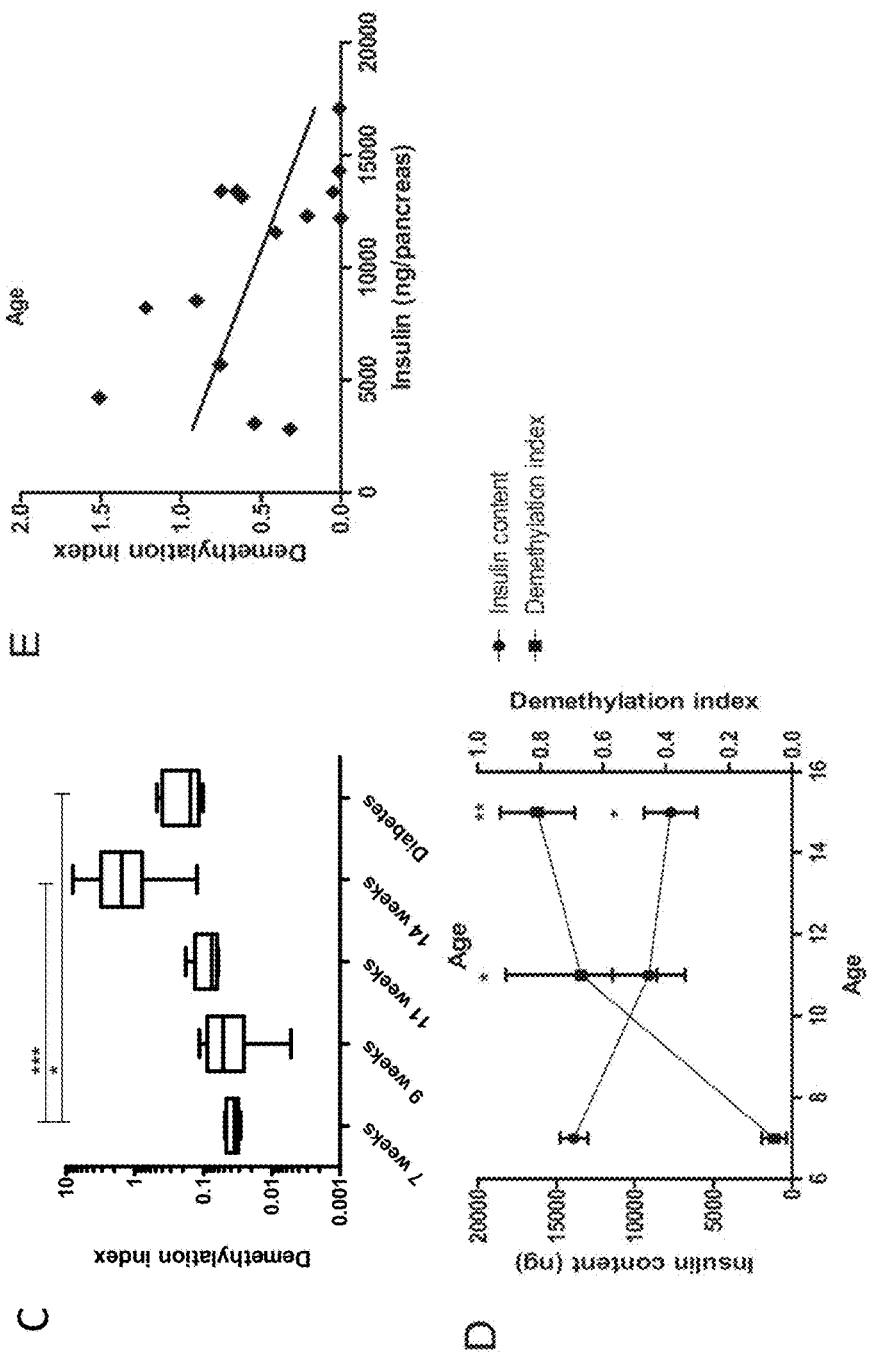

Next assessed was whether chronic β cell destruction could be detected in the NOD mouse model of spontaneous diabetes, a model of chronic autoimmunity in human T1D. NOD mice were challenged with an i.p. glucose tolerance test (IPGTT) beginning at 7 weeks of age, during which basal glucose levels were normal, and extending through the development of overt hyperglycemia (FIG. 5A). The IPGTTs revealed subtle changes in glucose tolerance beginning at 9 weeks of age that were statistically significantly different from the 7-week response only at 14 weeks (P<0.05) (FIG. 5B). The fasting glucose levels remained normal at all time-points (FIGS. 5A-5B) (24). The demethylation index increased significantly before the decline in insulin levels and before the increase in fasting glucose levels (P=0.0002) (FIG. 5C). At 14-15 weeks, the median demethylation index was increased by 21-fold (range, 3.2- to 211-fold; n=12) compared with the average of 7-week-old mice (P<0.01) (FIGS. 5C-5D). Interestingly, in 16- to 24-week-old mice with overt hyperglycemia, the index declined but was still elevated compared with that in the 7-week-old NOD mice (P<0.05).

Figure 6:
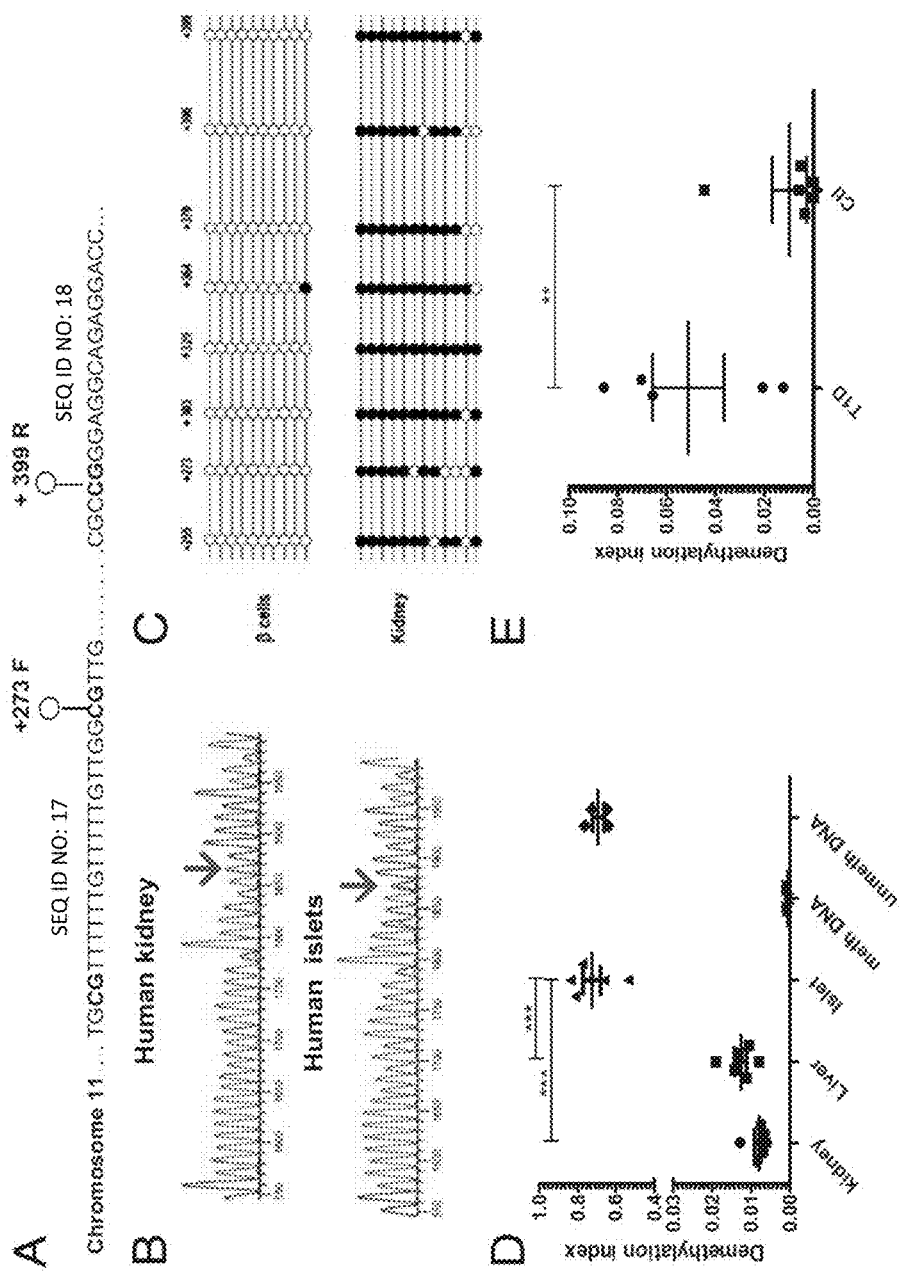
FIG. 6, comprising
Figure 7:
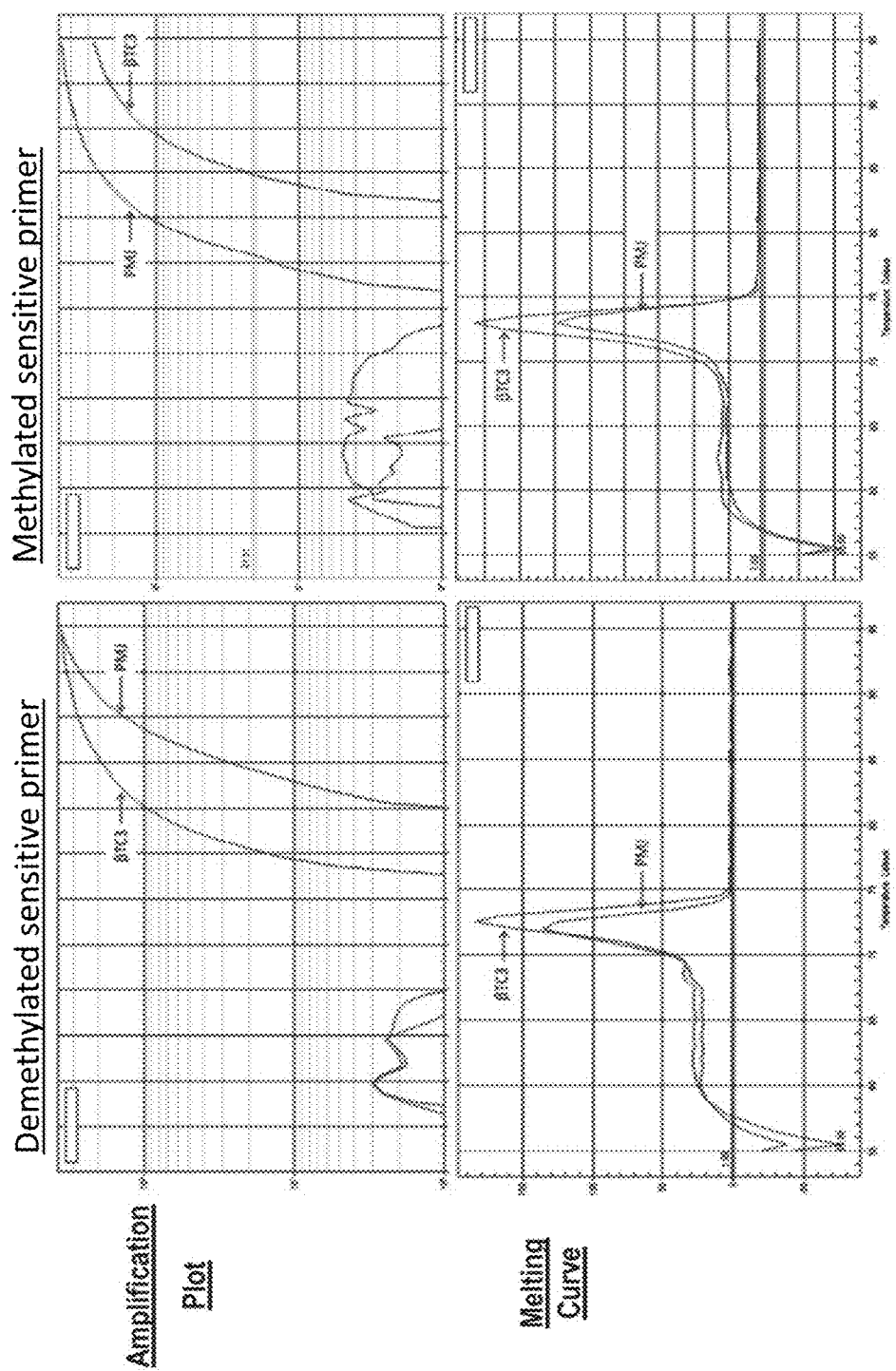
FIG. 7 depicts melting curves from the 2nd step PCR reactions. Real-time PCR data for methylated (left) and demethylated (right) dependent primers of PMJ and βTC3. The upper graphs depict amplification plots. The lower graphs depict melting curves. The primer specific for the demethylated sequence shows lower Ct values than the primer for the methylated sequence with DNA from βTC3 cells, whereas the opposite is seen with DNA from PMJ. A single experiment representative of three independent experiments is shown.

The range of increase in demethylation indices in the prediabetic mice was broad, possibly related to individual differences. To understand the relationships between β cell mass and the demethylation index, the relationship between total pancreatic insulin content and the demethylation index was investigated in a separate experiment with prediabetic NOD mice. A decline in pancreatic insulin content with age was found that was statistically lower at 15 week compared with 7-week-old NOD mice (P<0.05). At the same time, the demethylation index increased by 13-fold at 11 weeks compared with 7 weeks (P<0.05), and by 14-fold at 15 weeks (P<0.01) (FIG. 5D). To analyze the relationship between pancreatic insulin content and the demethylation index in individual mice, these two parameters were compared and found to be significantly correlated ($r^2$=0.28; P<0.05) (FIG. 5E). Taken together, these data show a link between an increased demethylation index and β cell loss. Demethylated Ins DNA is Increased in Human Islets and in Serum from Patients with New-Onset T1D A similar strategy was used to analyze demethylated insulin DNA in human tissues. Primers for the first step and nested PCR reactions were prepared from the analogous sequences in human INS on chromosome 11 (FIG. 6A and FIG. 8). Total DNA was isolated and used in the first-step PCR after bisulfite treatment.

The products of the first-step PCR were sequence and two peaks in the CpG site at nucleotide 2182036 (genome.ucsc.edu/cgi-bin/hgGateway; February 2009 GRCh37/hg19) in position +399 downstream from the transcription start site in the DNA from human islets were identified. This double peak corresponds to methylated and demethylated cytosines. Only a single peak, corresponding to methylated cytosine, was found in human kidney DNA (FIGS. 6A-6B).

Primary insulin-positive human β cells were sorted from dissociated islets by staining with the zinc selective dye FluoZin-3-AM and products of the first-step reaction from these cells were cloned, and the sequences compared with kidney cells (Jayamaran, 2011, Curr. Protoc. Cytom. 55:6.27.1-6.27.16). All of the clones (10 of 10) exhibited purified β cells demethylated at bp 273 and 399 in the insulin gene, compared with 0 of 12 clones from kidney (P<0.001) (FIG. 6C). Moreover, CpG sites were rarely demethylated in kidney (<25% of clones), and none of the clones from kidney exhibited demethylation at all of the CpG sites, whereas all sites but one were demethylated in all 10 clones sequenced from human β cells.

The demethylation index in DNA isolated from islets, kidney, and liver as well as in unmethylated and methylated synthetic DNA was compared (FIG. 6D). A significant increase in the demethylation index in islets (P<0.001) compared with liver (57-fold) and kidney (91-fold) was found. The demethylation index with islet DNA (0.729±0.05) was similar to the demethylation index with synthetic unmethylated DNA (0.70±0.03). The identity of products was verified by sequencing. The average interassay coefficient of variation from three separate analyses of this tissue DNA was 21.7%±6.4%.

The demethylation index in serum samples from patients with T1D (n=5; mean age, 10.8±1.02 years; range, 8-14 years) within the first year (mean duration of T1D, 7.0±1.30 months; range, 4-11 months) after diagnosis with healthy control subjects who were age-matched were compared, because demethylation might have been affected by islet growth in children (FIG. 6E). The demethylation index was significantly higher in the patients with T1D (P<0.02), and the average demethylation index in the nondiabetic subjects was similar to the index with DNA isolated from liver or kidney.

A similar analysis with second-step PCR primers that target bp +329 was also conducted. Analysis with this primer pair resulted in overall lower demethylation indices, but we found a similar significant increase in the demethylation index ($4.42 \times 10^{-4} \pm 2.07 \times 10^{-4}$ vs. $2.37 \times 10^{-6} \pm 1.81 \times 10^{-6}$) in this second cohort of subjects with recent-onset (i.e., first 1½ y) T1D (n=12) compared with healthy control subjects (n=11; P=0.015).

Demethylation Index in Human Patients with Recent Onset of Disease

Figure 11:
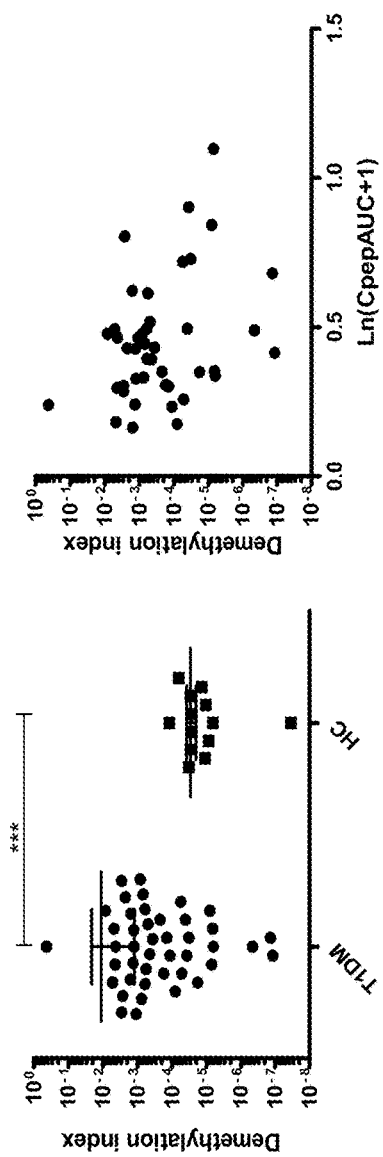
FIG. 11 depicts demethylation index in human patients with recent onset of disease.

The demethylation index of 43 subjects with recent onset (i.e. within 1 year of diagnosis) of disease was compared with the demethylation index of 13 healthy control subjects. The demethylation index was significantly higher in the subjects with disease and there was an inverse relationship between the demethylation index and the insulin secretory response to a mixed meal in these subjects (FIG. 11). In addition the coefficient of variation among repeated (4) sampling from 3 healthy control individuals was determined; the CV's ranged from 9.6%-12.8%.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting hypomethylated insulin DNA in a biological sample containing insulin DNA of a subject to determine whether the sample comprises insulin DNA of β cell origin, the method comprising:
obtaining a biological sample from the subject, wherein the biological sample is blood, serum or plasma obtained from outside of the subject's pancreas,
performing bisulfite treatment on the insulin DNA to form bisulfite-treated DNA,
amplifying said bisulfite-treated DNA to form amplified bisulfite-treated DNA,
sequencing the amplified bisulfite-treated DNA, and
detecting hypomethylated insulin DNA in the biological sample by determining the methylation status of each CpG dinucleotide in the amplified bisulfite-treated DNA, thereby determining a methylation status of the insulin DNA,
wherein when the methylation status of at least one of the CpG dinucleotides in the insulin DNA is determined to be unmethylated, the sample is determined to comprise hypomethylated insulin DNA, and
wherein when the methylation status comprises demethylation at one of more of the CpG dinucleotides at nucleotide positions 255, 273, 303, 329, 364, 370, 396, and 399 downstream of the transcription start site, the sample is determined to comprise insulin DNA of β cell origin.

2. The method of claim 1, wherein the step of sequencing the amplified bisulfite-treated DNA utilizes at least one technique selected from the group consisting of bisulfite sequencing, pyrosequencing of bisulfite-treated DNA, and dideoxy nucleotide sequencing.

3. The method of claim 1, wherein the subject is human.

4. The method of claim 1, wherein said step of amplifying said bisulfite-treated DNA utilizes at least one technique selected from the group consisting of: PCR, methylation-specific PCR, and real-time PCR.

5. The method of claim 4, wherein the PCR, real-time PCR or methylation-specific PCR uses at least one primer selected from the group consisting of SEQ ID NOS: 8-11.

6. The method of claim 1, further comprising the step of quantifying the amount of hypomethylated insulin DNA having the methylation status comprising demethylation at one of more of the CpG dinucleotides at nucleotide positions 255, 273, 303, 329, 364, 370, 396, and 399 downstream of the transcription start site, wherein the quantity of hypomethylated insulin DNA having said methylation status is an indicator of the severity of β cell death, wherein a higher said amount of hypomethylated insulin DNA having said methylation status indicates a greater severity of β cell death in the subject.

7. The method of claim 6, wherein the β cell death is associated with at least one disease or disorder selected from the group consisting of: pre-diabetes mellitus, diabetes mellitus, diabetes mellitus type 1, diabetes mellitus type 2, and gestational diabetes.

8. The method of claim 1, further comprising the step of quantifying the amount of hypomethylated insulin DNA having the methylation status comprising demethylation at one of more of the CpG dinucleotides at nucleotide positions 255, 273, 303, 329, 364, 370, 396, and 399 downstream of the transcription start site at a first time point and then at a second time point, and using said amount at the first time point and said amount at the second time point as an indicator of the progression of β cell death, wherein when the amount of hypomethylated insulin DNA having said methylation status at the second time point is greater than at the first time point, the β cell death in the subject is indicated as advancing, and wherein when the amount of hypomethylated insulin DNA having said methylation status at the first time point is higher than at the second time point, the β cell death in the subject is indicated as lessening.

9. The method of claim 8, wherein the β cell death is associated with at least one disease or disorder selected from the group consisting of: pre-diabetes mellitus, diabetes mellitus, diabetes mellitus type 1, diabetes mellitus type 2, and gestational diabetes.

10. The method of claim 1, further comprising the step of quantifying the amount of hypomethylated insulin DNA having the methylation status comprising demethylation at one of more of the CpG dinucleotides at nucleotide positions 255, 273, 303, 329, 364, 370, 396, and 399 downstream of the transcription start site at a first time point before a therapeutic regimen is applied and at a second time point during or after the therapeutic regimen is applied, and using said amount at the first time point and said amount at the second time point as an indicator of the effect of the therapeutic regimen on a subject's progression of β cell death, wherein when the amount of hypomethylated insulin DNA having said methylation status detected at the first time point is greater than the amount at the second time point, the indicated effect of the therapeutic regimen is to reduce the severity of the β cell death in the subject, and wherein when the amount of hypomethylated insulin DNA having said methylation status detected at the first time point is lower than the amount at the second time point, the indicated effect of the therapeutic regimen is not to reduce the severity of the β cell death in the subject.

11. The method of claim 10, wherein the β cell death is associated with at least one disease or disorder selected from the group consisting of: pre-diabetes mellitus, diabetes mellitus, diabetes mellitus type 1, diabetes mellitus type 2, and gestational diabetes.

12. The method claim 1, further comprising the step of quantifying the amount of hypomethylated insulin DNA having the methylation status comprising demethylation at one of more of the CpG dinucleotides at nucleotide positions 255, 273, 303, 329, 364, 370, 396, and 399 downstream of the transcription start site, and using said amount of hypomethylated insulin DNA having said methylation status as an indicator of the prognosis for the success of a β cell transplant, islet transplant, or pancreas transplant, wherein a greater amount of hypomethylated insulin DNA having said methylation status is an indicator of greater β cell death and a poorer prognosis and wherein a lower amount of hypomethylated insulin DNA having said methylation status is an indicator of lower β cell death and a better prognosis.

13. A method of detecting an indicator of β cell death by detecting hypomethylated insulin DNA in a subject according to the method of claim 1, comprising the step of detecting the indicator of β cell death when at least one of the CpG dinucleotides in the insulin DNA at nucleotide positions 255, 273, 303, 329, 364, 370, 396, and 399 downstream of the transcription start site is determined to be unmethylated.

14. A method of measuring the level of an indicator of β cell death by detecting hypomethylated β cell insulin DNA in a subject according to the method of claim 1, further comprising the step of quantifying the amount of hypomethylated insulin DNA having the methylation status comprising demethylation at one of more of the CpG dinucleotides at nucleotide positions 255, 273, 303, 329, 364, 370, 396, and 399 downstream of the transcription start site, and wherein a higher amount of hypomethylated insulin DNA having said methylation status indicates a higher level of β cell death.

15. A method of diagnosing a subject suspected of having β cell death by detecting hypomethylated insulin DNA in the subject according to the method of claim 1, further comprising the step of diagnosing the subject with β cell death when hypomethylated insulin DNA having the methylation status comprising demethylation at one of more of the CpG dinucleotides at nucleotide positions 255, 273, 303, 329, 364, 370, 396, and 399 downstream of the transcription start site is detected.

16. A method of diagnosing a subject suspected of having a disease or disorder associated with β cell death by detecting hypomethylated insulin DNA in the subject according to the method of claim 1, further comprising the step of diagnosing the subject with a disease or disorder associated with β cell death when hypomethylated insulin DNA having the methylation status comprising demethylation at one of more of the CpG dinucleotides at nucleotide positions 255, 273, 303, 329, 364, 370, 396, and 399 downstream of the transcription start site is detected, wherein the disease or disorder associated with β cell death is at least one selected from the group consisting of: pre-diabetes mellitus, diabetes mellitus, diabetes mellitus type 1, diabetes mellitus type 2, and gestational diabetes.

* * * * *

SEQUENCE LISTING

<160> NUMBER OF SEQ ID NOS: 18

<210> SEQ ID NO 1
<211> LENGTH: 43
<212> TYPE: DNA
<213> ORGANISM: Mus musculus

<400> SEQUENCE: 1

-continued

```
gtgtatttttt tattttttgtt ggttttgttt gttttttggg agt        43
```

<210> SEQ ID NO 2
<211> LENGTH: 41
<212> TYPE: DNA
<213> ORGANISM: Mus musculus

<400> SEQUENCE: 2

```
aaacttcctc ccaactccaa ttattccact tataaatcct c            41
```

<210> SEQ ID NO 3
<211> LENGTH: 25
<212> TYPE: DNA
<213> ORGANISM: Mus musculus

<400> SEQUENCE: 3

```
tttttgtggt ttttatttgg tagag                              25
```

<210> SEQ ID NO 4
<211> LENGTH: 21
<212> TYPE: DNA
<213> ORGANISM: Mus musculus

<400> SEQUENCE: 4

```
ttataaatcc tccacttcac g                                  21
```

<210> SEQ ID NO 5
<211> LENGTH: 21
<212> TYPE: DNA
<213> ORGANISM: Mus musculus

<400> SEQUENCE: 5

```
ttataaatcc tccacttcac a                                  21
```

<210> SEQ ID NO 6
<211> LENGTH: 28
<212> TYPE: DNA
<213> ORGANISM: Homo sapiens

<400> SEQUENCE: 6

```
ttagggtttt taaggtaggg tatttggt                           28
```

<210> SEQ ID NO 7
<211> LENGTH: 37
<212> TYPE: DNA
<213> ORGANISM: Homo sapiens

<400> SEQUENCE: 7

```
accaaaaaca acaataaaca attaactcac cctacaa                 37
```

<210> SEQ ID NO 8
<211> LENGTH: 27
<212> TYPE: DNA
<213> ORGANISM: Homo sapiens

<400> SEQUENCE: 8

```
gtggatgcgt tttttgtttt tgttggc                            27
```

<210> SEQ ID NO 9
<211> LENGTH: 25
<212> TYPE: DNA
<213> ORGANISM: Homo sapiens

-continued

```
<400> SEQUENCE: 9
caccctacaa atcctctacc tcccg                                          25

<210> SEQ ID NO 10
<211> LENGTH: 29
<212> TYPE: DNA
<213> ORGANISM: Homo sapiens

<400> SEQUENCE: 10
ttgtggatgt gttttttgtt tttgttggt                                      29

<210> SEQ ID NO 11
<211> LENGTH: 25
<212> TYPE: DNA
<213> ORGANISM: Homo sapiens

<400> SEQUENCE: 11
caccctacaa atcctctacc tccca                                          25

<210> SEQ ID NO 12
<211> LENGTH: 42
<212> TYPE: DNA
<213> ORGANISM: Mus musculus

<400> SEQUENCE: 12
gttggttttg tttgttttttt gggagtttaa atttatttag gt                      42

<210> SEQ ID NO 13
<211> LENGTH: 38
<212> TYPE: DNA
<213> ORGANISM: Mus musculus

<400> SEQUENCE: 13
ttctccaact aataaaaaaa acaaatacta atacaaca                            38

<210> SEQ ID NO 14
<211> LENGTH: 35
<212> TYPE: DNA
<213> ORGANISM: Mus musculus

<400> SEQUENCE: 14
ctacacaccc aagtcccgcc gtgaagtgga ggacc                               35

<210> SEQ ID NO 15
<211> LENGTH: 35
<212> TYPE: DNA
<213> ORGANISM: Mus musculus

<400> SEQUENCE: 15
ttatatattt aagtttcgtc gtgaagtgga ggatt                               35

<210> SEQ ID NO 16
<211> LENGTH: 35
<212> TYPE: DNA
<213> ORGANISM: Mus musculus

<400> SEQUENCE: 16
ttatatattt aagtttcgtt gtgaagtgga ggatt                               35

<210> SEQ ID NO 17
<211> LENGTH: 26
<212> TYPE: DNA
<213> ORGANISM: Homo sapiens
```

```
<400> SEQUENCE: 17
tgcgtttttt gttttgttg gcgttg                                                26

<210> SEQ ID NO 18
<211> LENGTH: 19
<212> TYPE: DNA
<213> ORGANISM: Homo sapiens

<400> SEQUENCE: 18
cgccgggagg cagaggacc                                                       19
```